United States Patent
Kraft et al.

(10) Patent No.: US 9,193,691 B2
(45) Date of Patent: Nov. 24, 2015

(54) METHODS FOR THE SYNTHESIS OF ACTIVATED ETHYLFUMARATES AND THEIR USE AS INTERMEDIATES

(71) Applicant: Mannkind Corp, Valencia, CA (US)

(72) Inventors: Kelly Sullivan Kraft, Poughquag, NY (US); John J. Freeman, New Fairfield, CT (US); Paul Serwinski, Bristol, CT (US); Vinnie Pavia, Valencia, CA (US); Otto Phanstiel, Oviedo, FL (US); Navneet Kaur, Danbury, CT (US)

(73) Assignee: MannKind Corporation, Valencia, CA (US)

( * ) Notice: Subject to any disclaimer, the term of this patent is extended or adjusted under 35 U.S.C. 154(b) by 106 days.

(21) Appl. No.: 13/834,106

(22) Filed: Mar. 15, 2013

(65) Prior Publication Data

US 2013/0289278 A1    Oct. 31, 2013

Related U.S. Application Data

(60) Provisional application No. 61/639,536, filed on Apr. 27, 2012.

(51) Int. Cl.
| | |
|---|---|
| *C07D 241/04* | (2006.01) |
| *C07D 241/08* | (2006.01) |
| *C07C 201/12* | (2006.01) |
| *C07C 67/39* | (2006.01) |
| *C07C 67/30* | (2006.01) |

(52) U.S. Cl.
CPC .............. *C07D 241/08* (2013.01); *C07C 67/30* (2013.01); *C07C 67/39* (2013.01); *C07C 201/12* (2013.01)

(58) Field of Classification Search
CPC .................................................... C07D 241/04
See application file for complete search history.

(56) References Cited

U.S. PATENT DOCUMENTS

| | | | |
|---|---|---|---|
| 3,407,203 A | 10/1968 | Buijle | |
| 5,352,461 A | 10/1994 | Feldstein | |
| 2004/0024180 A1 | 2/2004 | Drauz | |
| 2006/0041133 A1 | 2/2006 | Stevenson | |
| 2011/0158935 A1 | 6/2011 | Kraft | |

FOREIGN PATENT DOCUMENTS

| | | | |
|---|---|---|---|
| CN | 101851213 | | 10/2010 |
| CN | 101851213 A | * | 10/2010 |
| WO | 2012/109256 | | 8/2012 |

OTHER PUBLICATIONS

Utah Valley University. "Saponification." (c) 2009. Available from: <http://science.uvu.edu/ochem/index.php/alphabetical/s-t/saponification/printpage/>.*
Kaur et al., A Delineation of Diketopiperazine Self-Assembly Processes: Understanding the Molecular Events Involved in NE-(Fumaroyl)diketopiperazine of L-Lys (FDKP) Interactions; Molecular Pharmaceutics (2008) vol. 5, No. 2, 294-315.
Rosenmund et al., Diketopiperazines from Leuchs Anhydrides; Angew Chem internat. edit. vol. 9 (1970) No. 2.
International Search Report and Written Opinion for PCT/US2013/032162, mailed Jul. 1, 2013.
Byung Hyun Lee and Co. "Constituents of microbial iron chelators. Alternate Syntheses of N-hydroxy-L-ornithine derivatives and applications to the synthesis of rhodotorulic acid" Journal of Organic Chemistry, vol. 49, No. 13, Jan. 1, 1984, p. 2418-2423.
Written opinion from International Searching Authority for PCT/US2014/028228 (c) 2014.

* cited by examiner

*Primary Examiner* — Andrew D Kosar
*Assistant Examiner* — John S Kenyon
(74) *Attorney, Agent, or Firm* — Calfee, Halter & Griswold LLP

(57) ABSTRACT

Disclosed embodiments relate to improved methods for the synthesis of activated fumarate intermediates and their use in chemical synthesis. Disclosed embodiments describe the synthesis of activated fumarate esters including those derived from activating groups including: 4-nitrophenyl, diphenylphosphoryl azide, pivaloyl chloride, chlorosulfonyl isocyanate, p-nitrophenol, MEF, trifluoroacetyl and chlorine, for example, ethyl fumaroyl chloride and the subsequent use of the activated ester in situ. Further embodiments describe the improved synthesis of substituted aminoalkyl-diketopiperazines from unisolated and unpurified intermediates allowing for improved yields and reactor throughput.

12 Claims, 21 Drawing Sheets

(a)　　　　　　　　　　　(b)

(c)　　　　　　　　　　　(d)

(a)

(b)

METHODS FOR THE SYNTHESIS OF ACTIVATED ETHYLFUMARATES AND THEIR USE AS INTERMEDIATES

CROSS-REFERENCE TO RELATED APPLICATIONS

This provisional patent application makes no claim of priority to any earlier filings.

TECHNICAL FIELD

The present invention relates to compositions for delivering active agents, and particularly biologically active agents. Disclosed embodiments are in the field of chemical synthesis and more particularly are related to improved synthetic methods for the preparation of ethyl-4-nitrophenylfumarate and its use as a chemical intermediate.

BACKGROUND

Drug delivery is a persistent problem in the administration of active agents to patients. Conventional means for delivering active agents are often severely limited by biological, chemical, and physical barriers. Typically, these barriers are imposed by the environment through which delivery occurs, the environment of the target for delivery, or the target itself.

Biologically active agents are particularly vulnerable to such barriers. For example in the delivery to humans of pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically active agents would be the route of choice for administration to animals if not for biological, chemical, and physical barriers such as varying pH in the gastrointestinal (GI) tract, powerful digestive enzymes, and active agent impermeable gastrointestinal membranes. Among the numerous agents which are not typically amenable to oral administration are biologically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastrointestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), FEBS Letters, Vol. 62, pg. 60; and Hashimoto et al. (1979), Endocrinology Japan, Vol. 26, pg. 337.

However, broad spectrum use of drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can deliver a broad range of active agents. One class of delivery system that has shown promise is diketopiperazines (DKP). In particular, 3,6-bis-substituted-2,5-diketopiperazines have been shown to effectively deliver biologically active agents to the systemic circulation of the lung.

Depending on the DKP and the route of administration, the DKP molecule can require substitution and/or modification of the side chains attached to the diketopiperazine ring to optimize the profile of the excipient for the delivery route at hand. One such group is includes diketopiperazines with a substituted amino alkyl group, or so-called 3,6-aminoalkyl-2,5-diketopiperazines. Substitution of the side-chain amino group often involves reaction with an electrophile. Many factors enter into the choice of an appropriate electrophile, such as commercial availability, whether it is appropriate for large scale production or is difficult to isolate for subsequent reaction with the aminoalkyldiketopiperazine.

The introduction of a fumaroyl side chain onto, for example, a 3,6-aminoalkyl-2,5-diketopiperazine has proven especially advantageous as an excipient. However, the introduction of this fumaroyl moiety requires significant synthetic effort. One option for functionalization of the DKP utilizes the fact that the aminoalkyl groups may be used as nucleophiles in order to further modify the diketopiperazine excipients. Ethylfumaryl chloride (EFC) is known and available commercially, however, there are disadvantages to pharmaceutical scale use of the acid chloride. Some of the disadvantages, include, limited reactivity, purity, potential for backlogs in commercial availability etc. Therefore, it may be advantageous to increase the reactivity of the electrophilic site. One way to accomplish this is through the p-nitrophenol ester of ethyl fumarate, ethyl-4-nitrophenylfumarate or other activated ethyl fumarates.

Moreover, there are considerable costs and time pressures involved with any production scale chemical manufacturing endeavor, including that of excipients like the aforementioned diketopiperazines. Therefore, there is a need not only for excipients with optimal physico-chemical properties, but also for optimized production scale manufacturing of those chemicals. This must take into account not only raw material and reaction costs, but also reactor throughput and time expended in synthesizing the target molecule. The general approach for maximizing overall yield for a chemical process involves maximizing the yield and purity of each intermediate along the chemical pathway. This regularly suggests isolating and purifying each intermediate prior to subsequent reaction. By taking this approach the hope is that: a) by-products and unreacted starting materials from each step are prevented from interacting with later introduced intermediates or starting materials; and b) purification of the end target is simplified by having previously removed prior by-products, starting materials, etc. and thereby maximizing yield of the end target by reducing the amount of loss due to purification that could take place.

SUMMARY

This and other unmet needs of the prior art are met by compounds and methods as described in more detail below. The use of substituted 3,6-aminoalkyl-2,5-diketopiperazines as pharmaceutical excipients has shown considerable promise. Of particular interest are carboxy substituted aminoalkyl-diketopiperazines such as those described by Formula I ($R_1=R_2=COOR_3$).

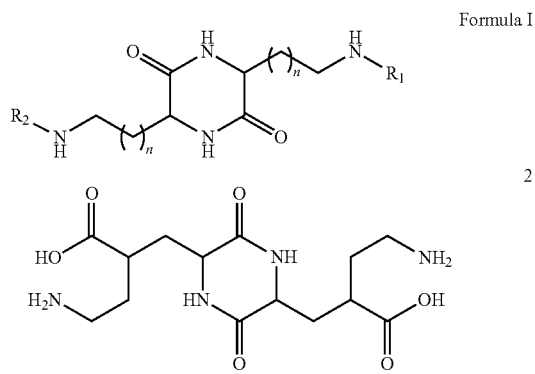

Formula I

2

Synthesis of carboxy substituted aminoalkyl-diketopiperazines ($R_1=R_2=RCOOH$) may proceed through an isolated aminoalkyl-diketopiperazine (for example the compound of the Formula 2) or an acid salt thereof (such as Formula 2). The amine is then reacted with an appropriate electrophile (for example ethyl-4-nitrophenylfumarate, 3) to give a substituted aminoalkyl-diketopiperazine (such as compound 4 R=Et) which, depending on the target molecule, may then undergo further functionalization or removal of protecting groups to give substituted aminoalkyl-diketopiperazines (such as compound 4 R=H).

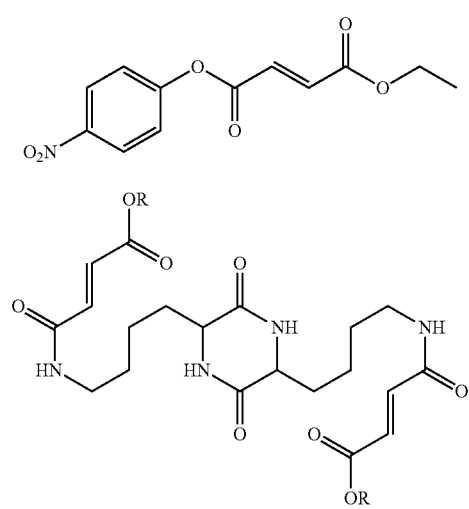

Generally, the aim of optimizing overall yield in a multi-step chemical synthesis is accomplished by isolation and purification of each intermediate molecule prior to subsequent reaction. This approach hopes to avoid loss of the final target due to: a) by-products of the previous steps reacting with intermediates or starting materials; and b) loss due to more complicated isolation and purification of the target molecule.

Disclosed embodiments provide methods for the synthesis of substituted diketopiperazine pharmaceutical excipients via use of in situ generated intermediates. The embodiments provide results which, counter to general thought, achieve higher yield and reactor throughput than traditional, isolate-and-purify-type methods. More specifically, embodiments show methods for the generation and use of fumaroyl intermediates in situ and without purification, as well as methods for the generation and use of aminoalkyl-diketopiperazines in situ and without isolation or purification.

In an embodiment, methods for the preparation of activated esters of mono-ethyl fumarate (MEF) are disclosed. Other embodiments relate to the generation of anhydrides of MEF and their use as intermediates. Further embodiments relate to the preparation and in situ use of activated esters of MEF. Further embodiments relate to the generation of ethyl-4-nitrophenylfumarate via the generation of a reactive salt of 4-nitrophenol. Further embodiments relate to the generation of activated esters of MEF from activated 4-nitrophenylesters. In an embodiment, an activating group, agent or reactant can be selected from a number of reactants, including, but not limited to diphenylphosphoryl azide, pivaloyl chloride, chlorosulfonyl isocyanate, p-nitrophenol, MEF, trifluoroacetyl and chlorine, for example, ethyl fumaroyl chloride.

Disclosed embodiments include a method for the synthesis of an activated ester of MEF comprising: providing a reactive electrophilic derivative of MEF; reacting an alcohol with an appropriate base and generating a salt of the alcohol, the base chosen from the group comprising: organic and inorganic metallic bases; and reacting the fumaric acid derivative with the sodium salt in an appropriate solvent. Further embodiments include methods where: the alcohol is 4-nitrophenol; the base is an inorganic metallic base; the base is sodium hydroxide; and where the salt is a sodium salt.

Disclosed embodiments include a method for the synthesis of an activated ester of MEF comprising: in a first reaction mixture, mixing a nucleophilic alcohol and an acid anhydride in an appropriate solvent; adding a proton scavenger; in a second reaction mixture, mixing MEF and a proton scavenger in an appropriate solvent; and adding the first mixture to the second mixture. Further embodiments include methods where: the alcohol is a phenol with an electron withdrawing substituent on the aryl ring; the alcohol is 4-nitrophenol; the proton scavenger is an organic amine; and wherein the solvent is a polar organic solvent.

Disclosed embodiments include a method for preparing a substituted aminoalkyl-diketopiperazine including: generating an aminoalkyl-diketopiperazine intermediate; generating an activated ester of MEF; reacting the aminoalkyl-diketopiperazine with the activated ester; and wherein the activated ester of ethylfumarate is reacted in situ without isolation or purification. Further embodiments include methods: further comprising the step of deprotecting the aminoalkyl-diketopiperazine prior to reaction with the activated ester; wherein the activated ester is a 4-nitrophenyl ester; wherein the step of generating the activated ester comprises: generating a mixed anhydride of MEF and another acid and reacting the mixed anhydride with an alcohol to produce the activated ester of MEF; and wherein the mixed anhydride is trifluoroacetyl-ethyl-fumarate.

BRIEF DESCRIPTION OF THE DRAWINGS

A better understanding of the exemplary embodiments of the invention will be had when reference is made to the accompanying drawings, wherein identical parts are identified with identical reference numerals, and wherein.

DETAILED DESCRIPTION

Generally, the aim of optimizing overall yield in a multi-step chemical synthesis is accomplished by isolation and purification of each intermediate molecule prior to subsequent reaction. This approach hopes to avoid loss of the final target due to: a) by-products of the previous steps reacting with intermediates or starting materials; and b) loss due to more complicated isolation and purification of the target molecule.

Disclosed embodiments provide methods for the synthesis of substituted diketopiperazine pharmaceutical excipients via use of in situ generated intermediates. The embodiments provide results which, counter to general thought, achieve higher yield and reactor throughput than traditional, isolate-and-purify-type methods. More specifically, embodiments show methods for the generation and use of fumaroyl intermediates in situ and without purification, as well as methods for the generation and use of aminoalkyl-diketopiperazines in situ and without isolation or purification. In embodiments disclosed herein, a method is provided for synthesizing an activated MEF in a simplified one-step process. In an embodiment, an activating group, agent or reactant can be selected from a number of reactants, including, but not limited to diphenylphosphoryl azide, pivaloyl chloride, chlorosulfonyl isocyanate, p-nitrophenol, MEF, trifluoroacetyl and chlorine, for example, ethyl fumaroyl chloride. In an exemplary embodiment, ethylfumaroyl chloride is reacted with a phenol containing an electron withdrawing moiety (such as p-nitrophenol) to form an activated ester of MEF, the ester is then used in situ as an electrophile to introduce the fumaryl moiety. In another aspect, an activated fumarate ester is generated using the sodium salt of a reactive alcohol such as 4-nitrophenol. This ester may also be used in situ in coupling reactions.

Figure 1:
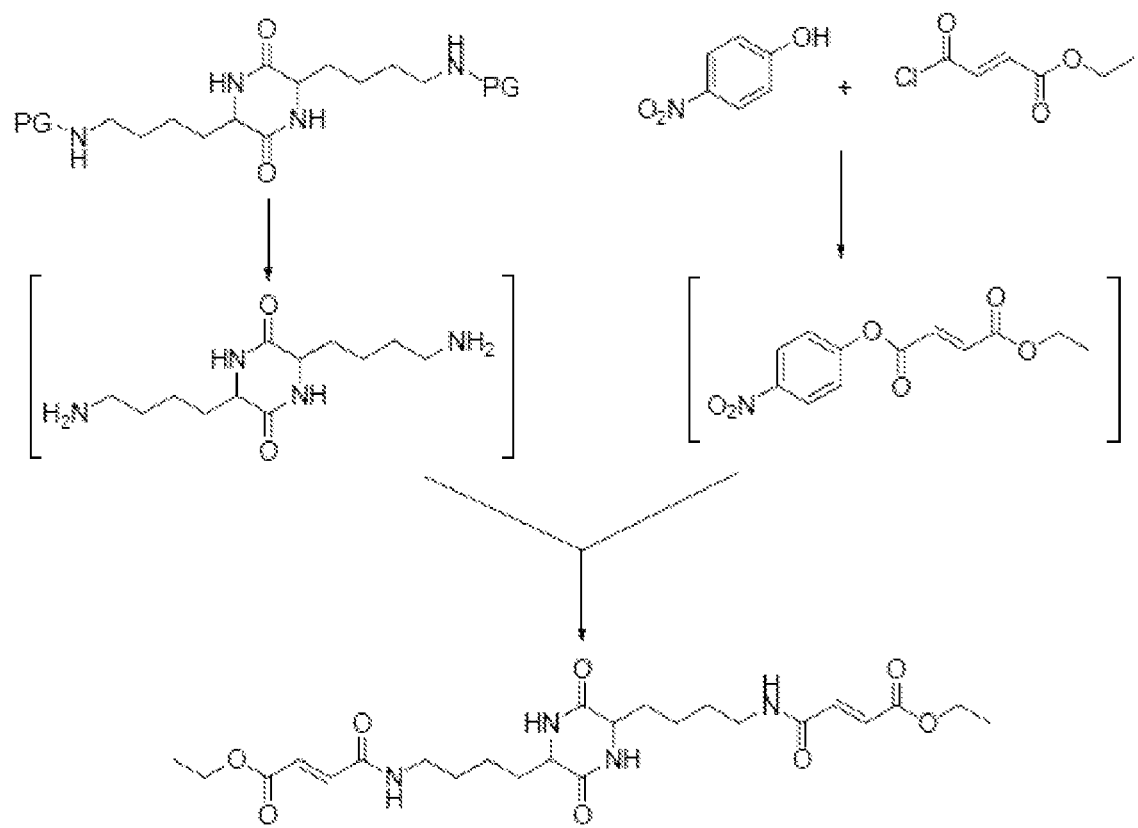
FIG. 1 is a scheme showing the synthesis of a substituted 3,6-aminoalkyl-2,5-diketopiperazine using an embodiment described herein.

Turning to the drawings for a better understanding, FIG. 1 shows a scheme for the generation of an ester substituted aminoalkyl-diketopiperazine. The synthesis of diketopiperazines such as this usually involves the coupling of the aminoalkyl-diketopiperazine with the activated ester with after isolation of both penultimate intermediates. Disclosed embodiments illustrate an improved method for the synthesis of this and similar diketopiperazines resulting in improved yields and reactor throughput.

EXAMPLES

Coupling of Ethyl Fumaroyl Chloride and 4-nitrophenol

A 1 L 4-neck round bottomed flask was charged with 11.20 g (80.51 mmol) of 4-nitrophenol, 90 mL of water, and 69 mL of acetone. While stirring under nitrogen, a solution of 12.80 g (120.8 mmol) of sodium carbonate in 90 mL of de-ionized water was added to the reaction. Ethyl fumaryl chloride (EFC) (17.0 mL, d=1.16 g/mL, 121 mmol) in 21 mL of acetone was added to the mixture using an addition funnel. An exotherm of 25-33° C. was observed during the EFC addition. As EFC addition progressed, the reaction mixture faded from yellow to colorless. At the end of the EFC addition, the reaction pH was 7-7.5. Approximately 15 minutes after the EFC addition was complete, the reaction was diluted with 450 mL of de-ionized water. A precipitate formed at 27° C. The mixture was held for 15 minutes, and then the solids were isolated, washed with de-ionized water (3×220 mL), and dried in a 50° C. vacuum oven for 1 hour. The product was analyzed for weight percent purity.

The coupling of EFC and 4-nitrophenol to generate ethyl-4-nitrophenylfumarate was evaluated in a total of eight experiments. The base and solvent system were held constant across experiments; the reaction and quench times were varied. When no time is provided for the reaction between EFC and 4-nitrophenol, the product yield appears to increase. However, this may be due to isolating excess sodium carbonate along with the product; the low wt % purities of these materials support this hypothesis. Reaction times of 15-60 minutes gave good ethyl-4-nitrophenylfumarate yield and purity (>96% and >94 wt %, respectively). Similarly, quench times of 15-45 minutes gave good product quality.

| Scale (mmol) | Time | Quench Time | Yield | % Weight |
|---|---|---|---|---|
| 14 | 45 | 30 | 97 | 96.22 |
| 14 | 60 | 45 | 96 | 96.28 |
| 36 | 15 | 15 | 99 | 98.55 |
| 36 | 15 | 15 | 97 | 90.08 |
| 36 | 0 | 15 | 101 | 87.5 |
| 36 | 30 | 15 | 122 | 87.94 |
| 36 | 0 | 30 | 112 | 82.85 |
| 81 | 15 | 15 | 96 | 94.94 |

Coupling of Ethyl Fumaryl Chloride and 4-nitrophenol Followed by In Situ Use with Deprotected DKP Part A (in situ ethyl-4-nitrophenylfumarate formation): A 1 L, 3-neck round bottom flask was equipped with a magnetic stirrer, temperature readout/controller, and an addition funnel with a nitrogen inlet. The exhaust gas was vented to a caustic scrubber. p-nitrophenol (9.18 g, 0.066 mol) and acetone (10 mL) were charged to the flask. Sodium hydroxide (2.90 g, 0.073 mol) dissolved in water (25 mL) was then added to the reaction mixture. During the sodium hydroxide addition, an exotherm of ~15° C. was observed and the reaction mixture changed from a clear yellow solution to yellowish orange suspension/slurry. After the addition was complete, the reaction mixture was cooled to 20° C. and EFC (8.78 g, 0.054 mol) in acetone (10 mL) was added via addition funnel over 5-10 minutes. During the EFC addition, an exotherm of ~15° C. was observed and the reaction mixture changed from orange to yellow; a solid was observed about 20 minutes after addition. The pH of the reaction mixture at the end of the EFC addition was 7-8. The reaction mixture was stirred at room temperature for an hour before additional acetone (30 mL) was added to dissolve the precipitated 022.

Part B (crude 4 formation): In a 250 mL Erlenmeyer flask, a solution of sodium hydroxide (8.82 g, 0.44 mol) in water (25 mL) was diluted with acetone (10 mL). Aminoalkyldiketopiperazine (Formula 1: $R_1=R_2=H$; n=3) (7.98 g, 0.021 mol) was charged to the Erlenmeyer flask. The neutralized diketopiperazine solution was charged to the round bottom flask containing the in situ ethyl-4-nitrophenylfumarate; the diketopiperazine flask was rinsed into the reactor with water (5 mL). The reaction mixture was heated to 50° C., held at temperature for one hour, cooled to ~30° C., and then quenched with water (50 mL). The resulting solids were collected by filtration, washed with water (2×100 mL) and acetone (2×100 mL) and dried in a vacuum oven at 50° C. overnight. The solids were analyzed using HPLC TM5466. Reaction yield, wt % purity, and area % purity were monitored.

Figure 2:
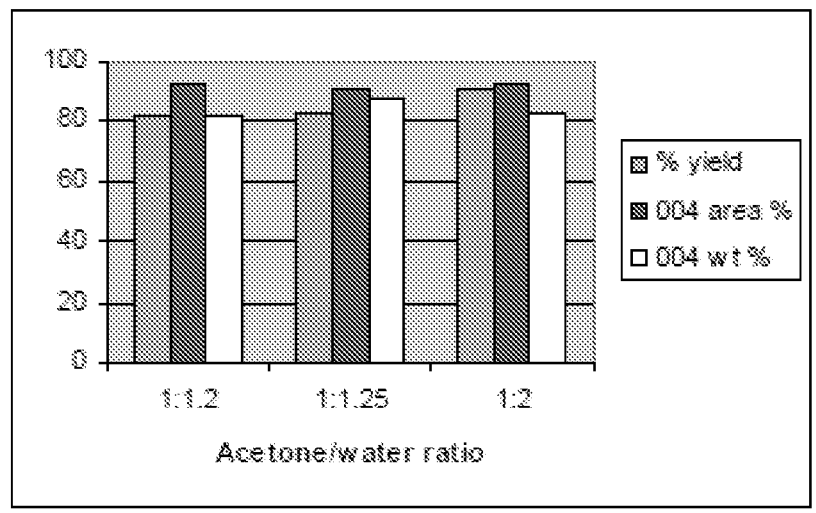
FIG. 2 shows results from experiments for a series of acetone/water mixtures that were explored to determine the optimum ratio for the reaction embodied in Part A.

FIG. 2 shows the results for a series of acetone/water mixtures that were explored to determine the optimum ratio for the reaction described in Part A (reaction between ethyl fumaroyl chloride and p-nitrophenol). The reaction does not proceed well in the absence of water. The results suggest that an acetone/water ratio of 1:1.25 provides a balance of high yield and purity. This is surprising as sodium hydroxide in water is a common method of saponification of esters but the ester forms and remains for future reaction.

Figure 3:
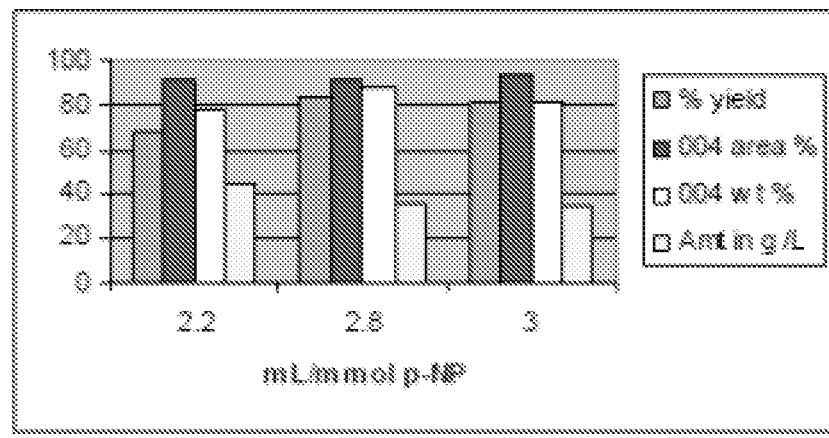
FIG. 3 is a graph showing the effects of the p-nitrophenol (p-NP) reactant concentration on quality of compound of the Formula 4 obtained.

FIG. 3 shows a graph of the results of reaction concentration on quality of 4 obtained. The intermediate conditions tested (2.8 mL solvent/mmol p-NP) gave a good balance of substituted aminoalkyl-diketopiperazine yield, purity, and reactor throughput. At high concentration, reactor throughput increased, but substituted aminoalkyl-diketopiperazines yield and purity suffered; at low concentration, wt % purity was slightly lower. The intermediate concentration tested yielded about 36 g of 4 (R=Et) was per 1 L of reactor space, about 30% better throughput than the conventional reaction.

Figure 4:
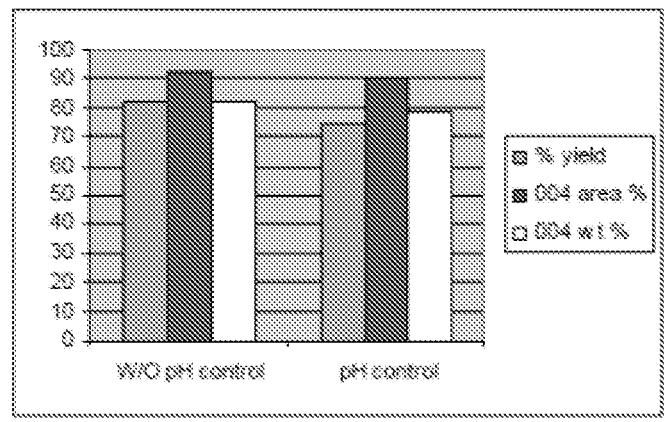
FIG. 4 is a graph showing the effects of pH control of Part A [same as above] reaction versus no pH control during the reaction.

FIG. 4 shows a graph of the results of controlling the pH of Part A reaction versus no pH control during the reaction. No significant difference in 4 yield or purity was obtained when reaction pH was controlled at 7.5 during EFC addition versus experiments where pH was not controlled.

Figure 5:
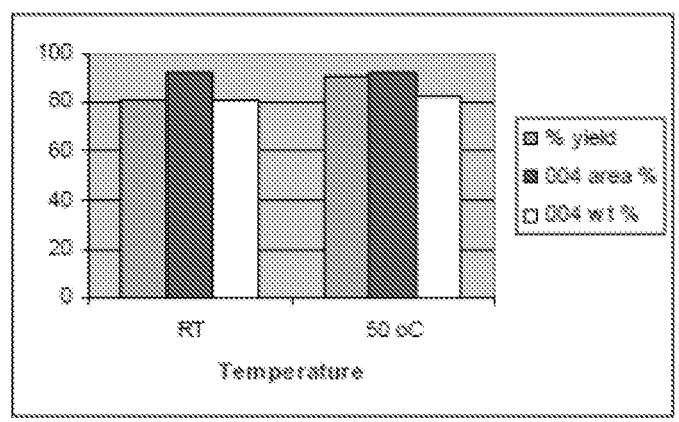
FIG. 5 shows the results from experiments comparing quality of product produced from Part B with reaction temperature at ambient versus elevated temperatures to 50° C.

FIG. 5 shows the results of comparing quality of product produced from Part B with reaction temperature at ambient versus elevated to 50° C. The results indicate that elevated temperatures provide better quality.

These studies demonstrated that EFC and p-NP can be combined to form an activated ester, then treated with aminoalkyl-diketopiperazines using sodium hydroxide as a base, to form crude substituted aminoalkyl-diketopiperazines in yields and purities comparable to known processes (isolating the penultimate intermediates and utilizing $Na_2CO_3$ for the final coupling), and with better reactor throughput. Results with sodium hydroxide were comparable to those obtained using sodium carbonate.

In Situ TFA-DKP Deprotection Followed by In Situ Use of ethyl-4-nitrophenyl fumarate:

Part A (in situ ethyl-4-nitrophenylfumarate formation): A 1 L, 3-neck round bottom flask was equipped with a magnetic stirrer, temperature readout/controller, and an addition funnel with a nitrogen inlet. The exhaust gas was vented to a caustic scrubber. p-Nitrophenol (9.18 g, 0.066 mol) and acetone (10 mL) were charged to the flask. Sodium hydroxide (2.90 g, 0.073 mol) dissolved in water (25 mL) was then added to the reaction mixture. During the sodium hydroxide addition, an exotherm of ~15° C. was observed and the reaction mixture changed from a clear yellow solution to a yellowish orange suspension/slurry. After the addition was complete, the reaction mixture was cooled to 20° C. and EFC (8.78 g, 0.054 mol) in acetone (10 mL) was added via addition funnel over 5-10 minutes. During the EFC addition, an exotherm of ~15° C. was observed and the reaction mixture changed from yellowish orange to a yellow suspension/slurry. The reaction mixture pH at the end of the EFC addition was 7-8. The reaction mixture was stirred at room temperature for an hour before additional acetone (15 mL) was added to dissolve the precipitated ethyl-4-nitrophenylfumarate.

Part B (crude 4 formation): A 250 mL round bottom flask was charged with the protected diketopiperazine (Formula 1, $R_1=R_2=$TFA; n=3, TFA-DKP) (9.68 g, 0.022 mol) and acetone (25 mL). Sodium hydroxide (2.16 g, 0.054 mol) dissolved in water (30 mL) was added to the TFA-DKP slurry/suspension. The mixture was stirred for 30 minutes at room temperature. The resulting clear, yellow solution was added to the flask containing the in situ ethyl-4-nitrophenylfumarate. The TFA-DKP flask was rinsed into the reactor with water (10 mL). The reaction mixture was heated to 45° C., held at temperature for one hour, cooled to ~30° C., and quenched with water (50 mL). The resulting solids were collected by filtration, washed with water (2×100 mL) and acetone (2×100 mL) and dried in a vacuum oven at 50° C. overnight. The solids were analyzed using HPLC TM5466. Reaction yield, wt % purity, and area % purity were monitored.

Figure 6:
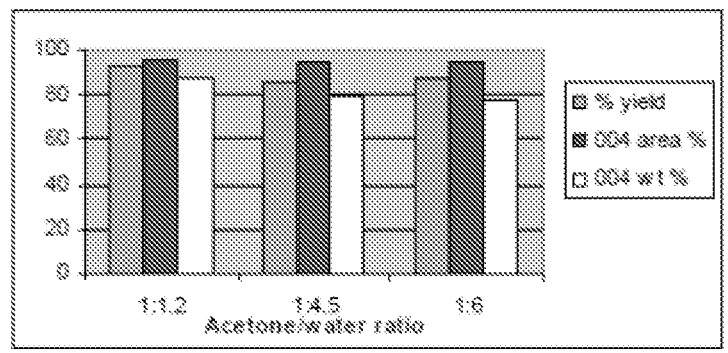
FIG. 6 a graph displaying the results obtained when varying the acetone/water ratios for the TFA deprotection of the diketopiperazine intermediate.

FIG. 6 shows a graph displaying the results obtained when varying the acetone/water ratios for the TFA deprotection of the diketopiperazine intermediate. The results suggested that an acetone/water ratio of 1:1.12 for the TFA-DKP resulted in the highest 4 (R=Et) yield and purity.

Figure 7:
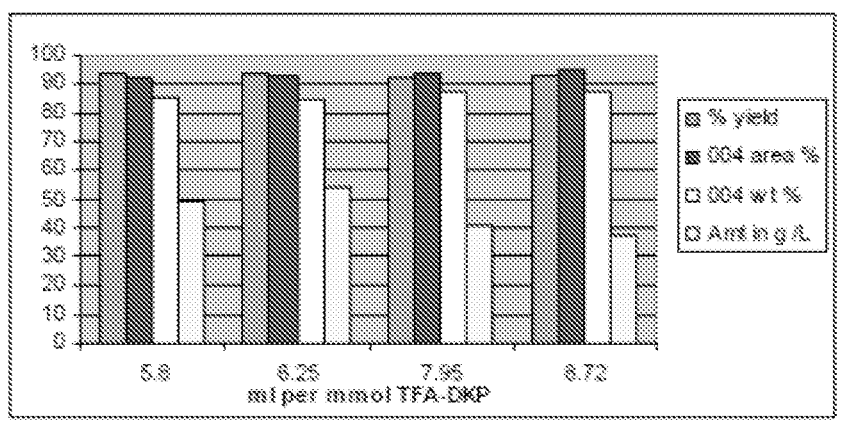
FIG. 7 a graph depicting data on the characteristics of compound of the Formula 4 when the reaction concentration is varied during the TFA deprotection step.

FIG. 7 shows a graph depicting the results of 4 quality when reaction concentration is varied during the TFA deprotection step. One of the intermediate conditions tested (7.95 mL solvent/mmol TFA-DKP) gave the best balance of 4 (R=Et) yield, purity, and reactor throughput. At higher concentration, reactor throughput was increased, but 4 (R=Et) wt % purity suffered; lower concentrations gave comparable yield and purity but poorer reactor throughput. A reaction concentration of 7.95 mL solvent/mol TFA-DKP gives ~40 g of 4 per 1 L of reactor space, about 40% better throughput than the current 4 (R=Et) reaction.

Figure 8:
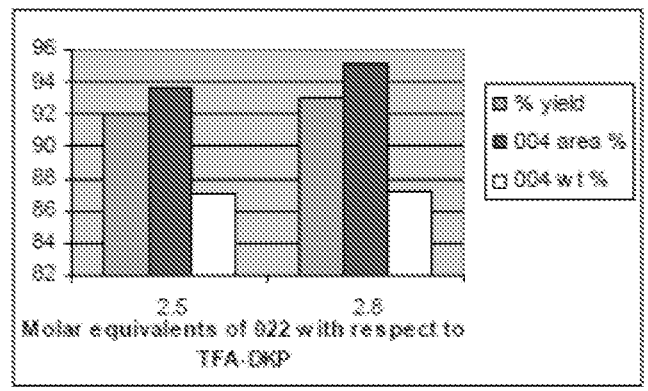
FIG. 8 is a graph depicting results comparing the charge of ethyl-4-nitrophenylfumarate on quality of compound of the Formula 4 obtained by a reaction embodiment disclosed herewith.

FIG. 8 is a graph of the results comparing the charge of ethyl-4-nitrophenylfumarate on quality of 4 obtained. The results indicate that there is no significant increase in overall quality when increasing the charge above 2.5 molar equivalents.

Figure 9:
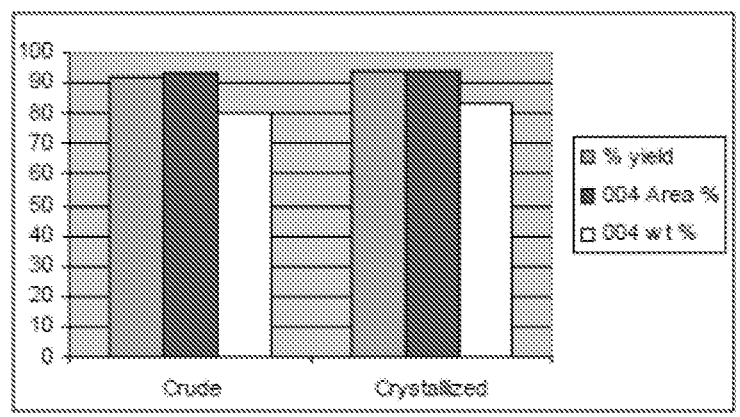
FIG. 9 is a graph depicting results obtained using either crude or recrystallized TFA-DKP when forming the compound of Formula 4.

FIG. 9 is a graph of the results obtained using either crude or recrystallized TFA-DKP when forming 4. The results indicate that intermediate TFA-DKP purity had a negligible effect on 4 quality.

These studies demonstrated that in situ ethyl-4-nitrophenylfumarate can be coupled with deprotected TFA-DKP using sodium hydroxide as the base. Compared to the current process, the best conditions identified in this study give 4 in comparable purity but with better yield and reactor throughput (40% more).

Figure 10:
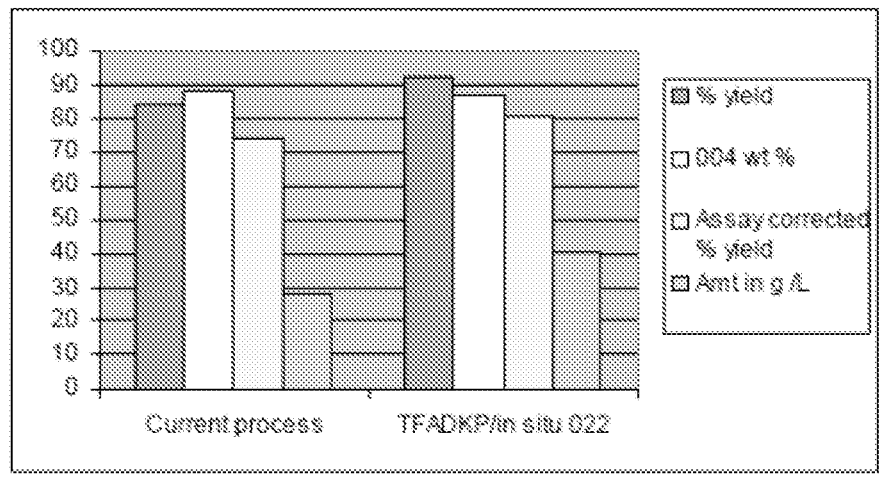
FIG. 10 is a graph comparing the compound of the Formula 4 overall quality obtained using a conventional method versus employing the in situ methodology described herein.

FIG. 10 is a graph comparing 4 overall quality obtained using a conventional method versus employing the in situ methodology. From this graph it is clear that the in situ scheme generates a higher quality product and significantly increases reactor throughput.

The following table shows the results from coupling ethyl-4-nitrophenylfumarate with an aminoalkyl-diketopiperazine. Bottom six reactions were carried out using in situ ethyl-4-nitrophenylfumarate, using EFC p-NP and TFA-DKP.

| Moles of diketopiperazine | Base | % Yield (corrected) | Mass from 1 L flask |
|---|---|---|---|
| .053 | $Na_2CO_3$ | 88.9 | 28 |
| .085 | $Na_2CO_3$ | 84 | 36.37 |
| .022 | NaOH | 90 | 35.6 |
| .022 | NaOH | 93 | 37 |
| .028 | NaOH | 91 | 47 |
| .022 | NaOH | 83 | 35.8 |
| .028 | NaOH | 82 | 46 |
| .028 | NaOH | 90 | 47 |
| .028 | NaOH | 73 | 42 |
| .028 | NaOH | 90 | 47 |
| .028 | NaOH | 94 | 53.84 |
| .028 | NaOH | 99 | 56.68 |
| .022 | NaOH | 100 | 44 |
| .022 | NaOH | 94 | 41.52 |
| .022 | NaOH | 92 | 40.32 |
| .028 | NaOH | 113 | 64.67 |

Example 4

Figure 11:
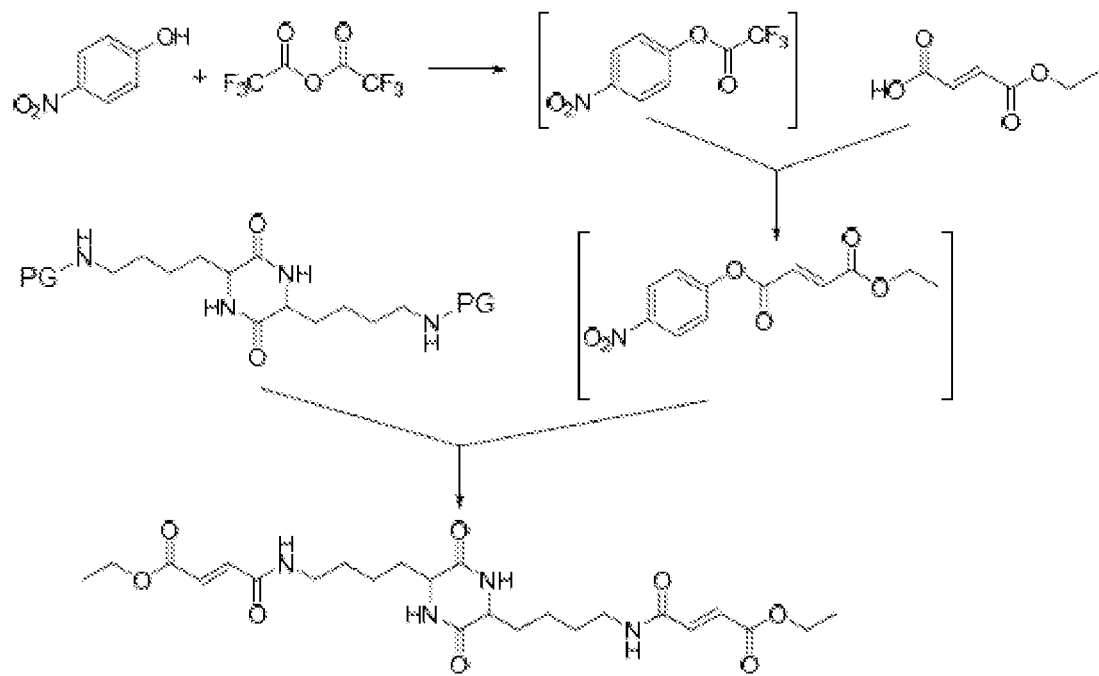
FIG. 11 is a chemical scheme showing an embodiment of a synthesis for a substituted aminoalkyl-diketopiperazine.

Experimental Preparation of 4 from MEF, TFAA and p-NP, NaOH for Coupling FIG. 11

Part A: A 250 mL 3-neck round bottom flask was equipped with a magnetic stirrer, a temperature readout/controller, and an addition funnel with a nitrogen head. The exhaust gas was vented to a caustic scrubber. The flask was charged with p-nitrophenol (p-NP, 10 g) and trifluoroacetic anhydride (TFAA, 16.61 g, 11 mL) and stirring was initiated. The resulting yellow slurry was treated with triethylamine (TEA, 600 µL). An exotherm of ~12° C. was observed after the TEA addition. The solution was stirred for about 30 minutes (until clear, an indication that formation was complete).

Part B (in situ ethyl-4-nitrophenylfumarate formation): A 250 mL 4-neck round bottom flask was equipped with a magnetic stirrer, a temperature readout/controller, an addition funnel with a nitrogen head and a reflux condenser. Monoethyl fumarate (MEF, 10.36 g) and acetone (9 mL) were charged to the flask. TEA (16.33 mL) was charged to the flask; an exotherm of ~15° C. was observed after the TEA addition. The resulting clear solution was cooled to 20° C. and the Part A solution was slowly added via addition funnel. The reaction temperature was maintained below 30° C. for the duration of the addition. The Part A flask was rinsed with acetone (3 mL), and the rinse added to the reaction flask. The reaction mixture was stirred for 30 minutes while maintaining the temperature between 20-30° C.

Part C (crude 4 (R=Et) formation): A 250 mL round bottom flask was charged with TFA-DKP (12.66 g) and acetone (25 mL). Sodium hydroxide (2.83 g) dissolved in water (30 mL) was added to the TFA-DKP slurry. The mixture was stirred at room temperature for about 30 minutes. The resulting clear, yellow solution was added to the flask containing the in situ ethyl-4-nitrophenylfumarate. The TFA-DKP flask was rinsed into the reactor with water (10 mL), and additional acetone (23 mL) and water (35 mL) were charged to the reaction mixture. The reaction mixture was heated to 45° C., held at temperature for one hour, cooled to ~30° C., quenched with water (50 mL) and stirred for additional 30 minutes. The resulting solids were collected by filtration, washed with water (2×100 mL) and acetone (2×100 mL) and dried in a vacuum oven at 50° C. overnight. The solids were analyzed using HPLC TM5466. Reaction yield, wt % purity, and area % purity were monitored.

In situ ethyl-4-nitrophenylfumarate was first generated from MEF and p-nitrophenyl trifluoroacetate, then coupled with deprotected TFA-DKP (2). The resulting crude 4 (R=Et) was obtained in 63% yield and 85 wt % purity. The initial conditions tested gave ~36 g of 4 per 1 L of reactor space, about 35% better throughput than the current process.

Substituting THF for acetone gave lower product yield, but comparable purity; the trans isomer content was elevated in this sample. Use of additional TFAA in the in situ ethyl-4-nitrophenylfumarate formation step failed to improve 4 (R=Et) yield or purity.

| Sample ID | TFAA Equivalents | Solvent | % Yield | g per 1 L flask | % Trans | % Wt | % Area |
|---|---|---|---|---|---|---|---|
| D733-47A | 1.1 | Acetone | 63 | 36.4 | 52.97 | 84.73 | 91.79 |
| D733-47T | 1.1 | THF | 38 | 21.56 | 71.45 | 84.62 | 88.15 |
| D733-67 | 1.25 | Acetone | 23 | 13.22 | 59.31 | 56.17 | 51.25 |

From this table it is clear that the in situ generation and use of the activated MEF gave good yield and, more importantly, improved throughput.

Example 5

A 500 mL, 3-neck round bottom flask was equipped with a magnetic stirrer, temperature readout/controller, and an addition funnel with a nitrogen inlet. The exhaust gas was vented to a caustic scrubber. Monoethyl fumarate (MEF, 5 g), dry dichloromethane or THF (10 mL), and triethylamine (TEA, 12 mL) were charged to the flask. An exotherm was observed during the TEA addition. The clear reaction mixture was cooled to 5° C. in an ice bath. A solution of chlorosulfonyl isocyanate (CSI, 4.96 g) in 10 mL of dry dichloromethane was added over 20-30 minutes. After the addition was complete, the reaction mixture was held below 10° C. for 3 hours. For reactions using DCM, the crude MEF anhydride was isolated by removing the solvent in vacuo. For reactions using THF as the solvent, the MEF anhydride was used without further manipulation.

A 500 mL 3-neck round bottom flask was equipped with a magnetic stirrer, temperature readout/controller, and an addition funnel with a nitrogen head. The exhaust gas was vented to a caustic scrubber. The flask was charged with 2 (5.47 g) and a solution of sodium carbonate (8.90 g) in water (80 mL). The activated anhydride obtained in step 1 was dissolved in THF (80 mL), and added to the flask. The reaction mixture was stirred at room temperature overnight. The resulting solids were collected by filtration, washed with water (50 mL) and acetone (20 mL) and dried in a vacuum oven at 50° C. overnight. The solids were analyzed using HPLC TM5466. Reaction yield, wt % purity, and area % purity were monitored. Assay-corrected yield was calculated by multiplying the yield by the wt % purity.

Figure 12:
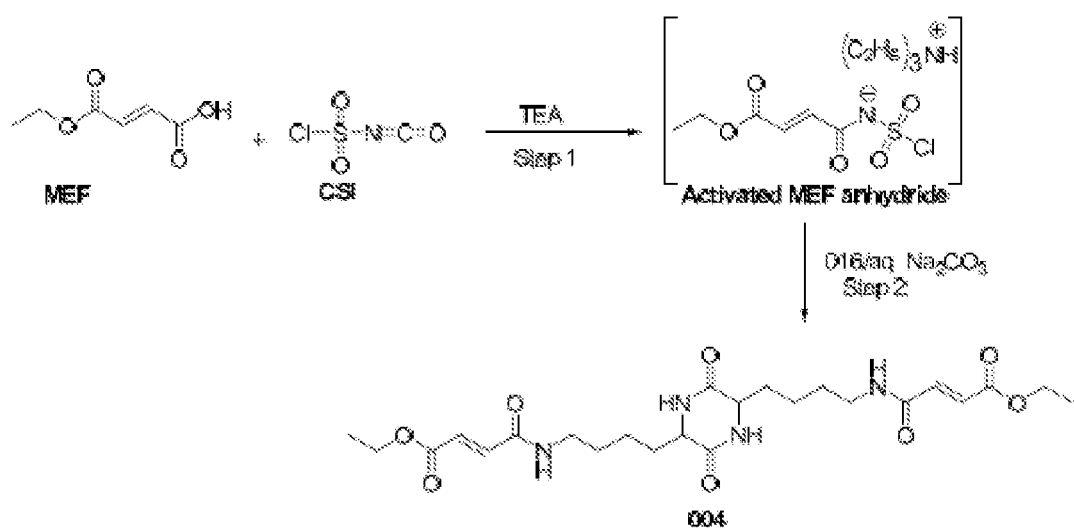
FIG. 12 is a chemical scheme showing the preparation of an activated MEF mixed anhydride followed by addition to an aminoalkyl-diketopiperazine.

FIG. 12 shows a chemical scheme for the generation of an activated MEF anhydride and subsequent reaction with a diketopiperazine.

Figure 13:
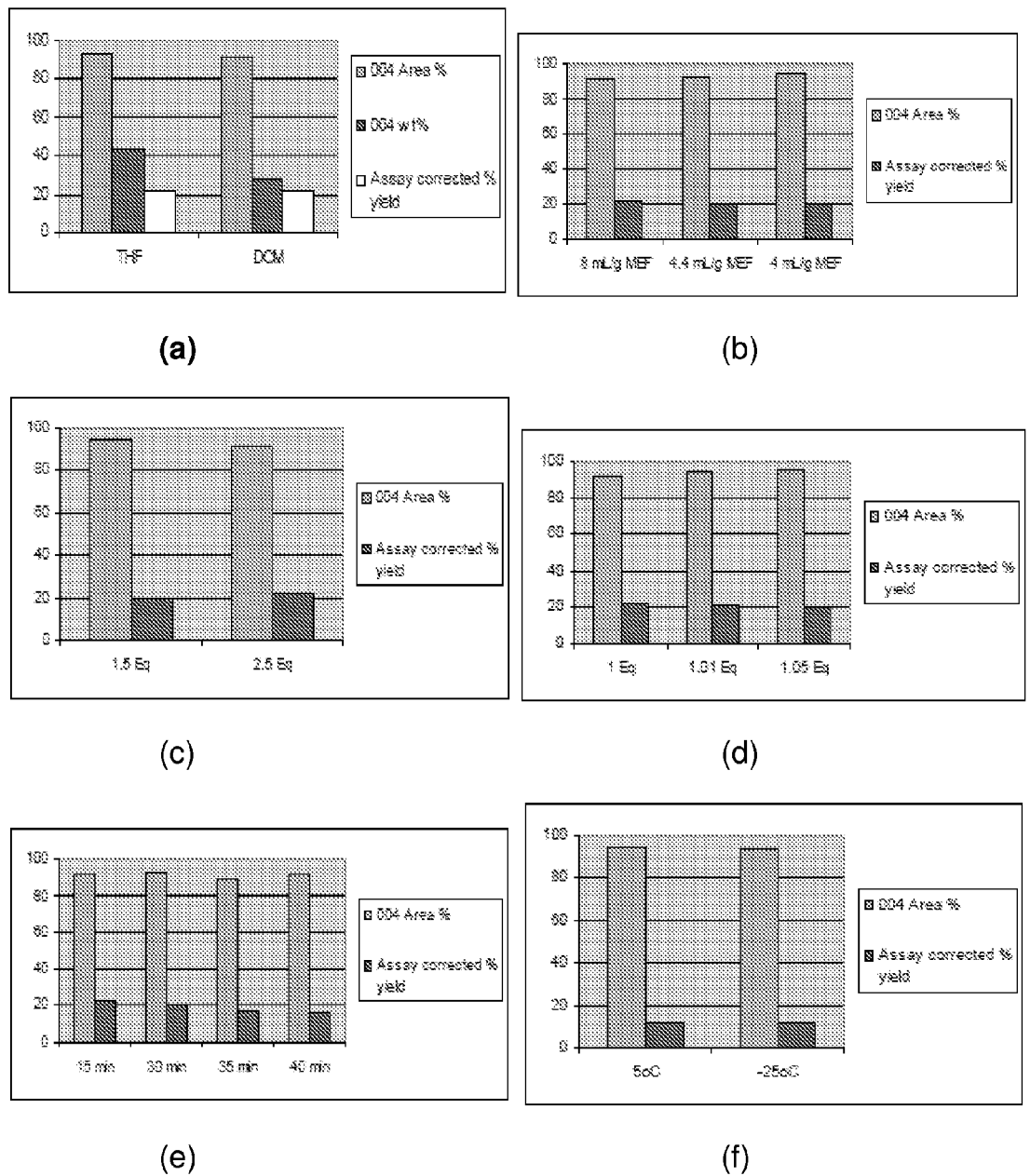
FIG. 13a-f shows tables of data related to anhydride formation under different conditions: (a) solvent; (b) concentration; (c) equivalents of TEA; (d) equivalents of CSI; (e) time for CSI addition; and (f) reaction temperature FIG. 14 a-e shows tables of data related to substituted aminoalkyl-diketopiperazine formation under varied conditions: (a) base; (b) solvent; (c) THF/water ratio; (d) reaction time/temperature; (e) effect of addition order.

FIG. 13a-f shows the results for MEF anhydride formation under varied conditions. Solvent, reaction concentration, amounts of TEA and CSI, addition time, and addition temperature were explored. FIG. 13a suggests that THF gives MEF activated anhydride in higher wt % purity than DCM and comparable assay-corrected yield. The other tested parameters (FIGS. 13b-f) did not affect assay-corrected yield or area % purity.

FIG. 14a-e shows the results for using the CSI-MEF anhydride and an aminoalkyl-diketopiperazine. The MEF activated anhydride was formed in situ using THF as the solvent, and then added to a basic solution of 2 to generate 4 (R=Et).

Figure 14:
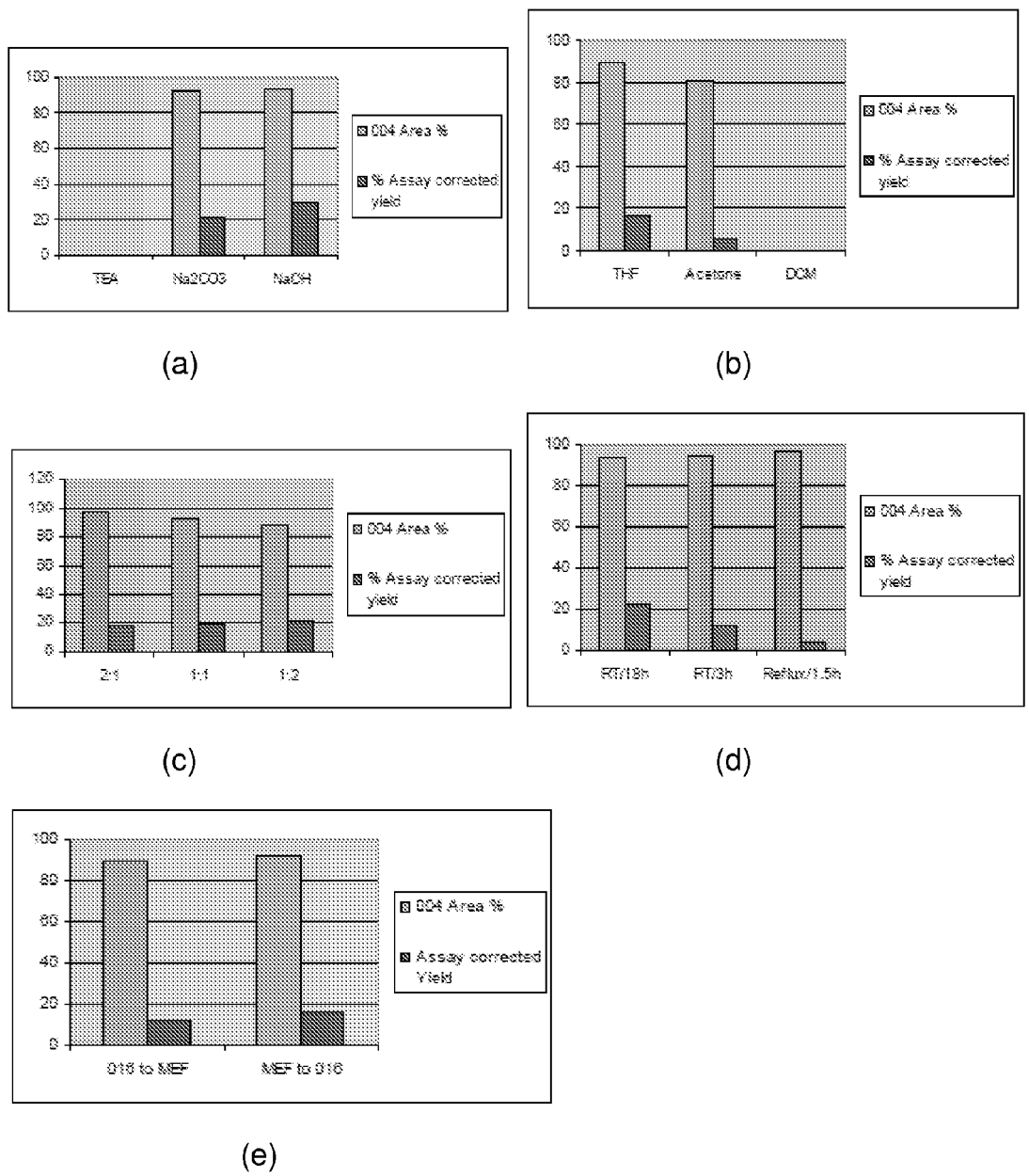

Three bases were evaluated: triethylamine, sodium carbonate and sodium hydroxide and the results shown in FIG. 14a. Sodium hydroxide produced 4 (R=Et) in higher assay-corrected yield than sodium carbonate; triethylamine was not suitable for this reaction because no material was obtained after a 72 hour reaction time.

Three solvents were evaluated: THF, DCM and acetone and the results shown in FIG. 14b. THF gave 4 (R=Et) in higher assay-corrected yield and purity than the other tested solvents. In addition, several different water/THF mixtures were explored because the reaction did not proceed well in the absence of water. However, the addition of water did not appear to improve yield or product quality (FIG. 14c).

Different reaction time and temperature combinations were also explored. High reaction temperature gave little 4; at room temperature, assay-corrected yields were increased with increasing time up to 18 hrs (FIG. 14d).

Figure 15:
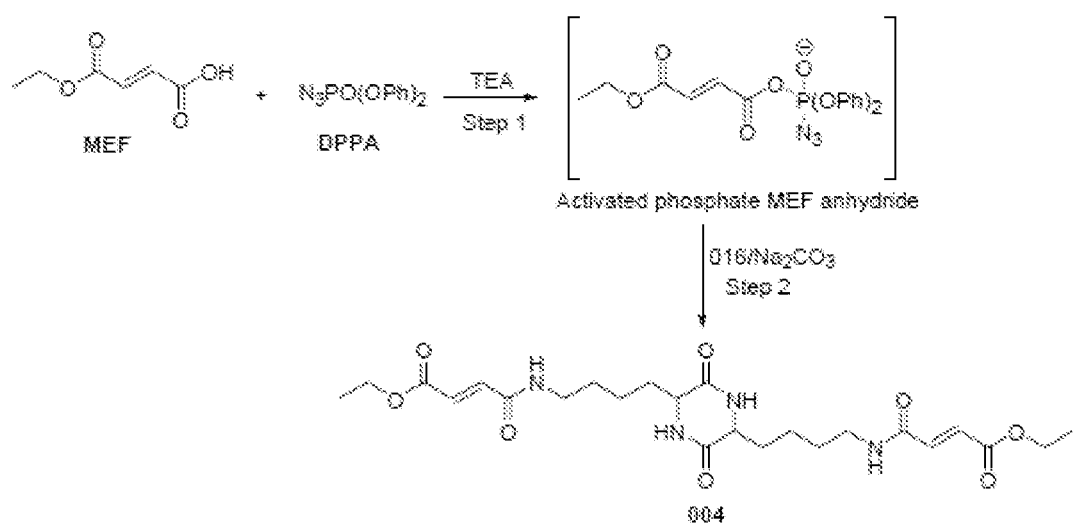
FIG. 15 shows a chemical scheme for the generation of 4 (R=Et) via an activated phosphate anhydride of MEF.

FIG. 15 shows a chemical scheme for the generation of an activated MEF anhydride and subsequent reaction with a diketopiperazine.

Example 4 (R=Et) Preparation Using an Activated MEF Phosphate Anhydride

A 500 mL, 3-necked round bottom flask was equipped with a magnetic stirrer, temperature readout/controller, and addition funnel with a nitrogen head. The exhaust gas was vented to a caustic scrubber. Mono-ethyl fumarate (MEF, 5 g), THF (15 mL), and triethylamine (TEA, 10 mL) were charged to the flask. An exotherm was observed during the TEA addition. Diphenylphosphoryl azide (DPPA, 9 mL) was added to the reaction mixture, followed immediately by the addition of 2 solution (28.21 g) dissolved in a solution of sodium carbonate (18.23 g) and water (60 mL). The flask containing the 016 was rinsed into the reaction mixture with water (10 mL). The reaction mixture was stirred at room temperature overnight. The resulting solids were collected by filtration, washed with water (2×100 mL) and acetone (2×50 mL) and dried in a vacuum oven at 50° C. overnight. The solids were analyzed using HPLC TM5466.

Parameter screen for 4 (R=Et) syntheses via activated MEF phosphate anhydride

Figure 16:
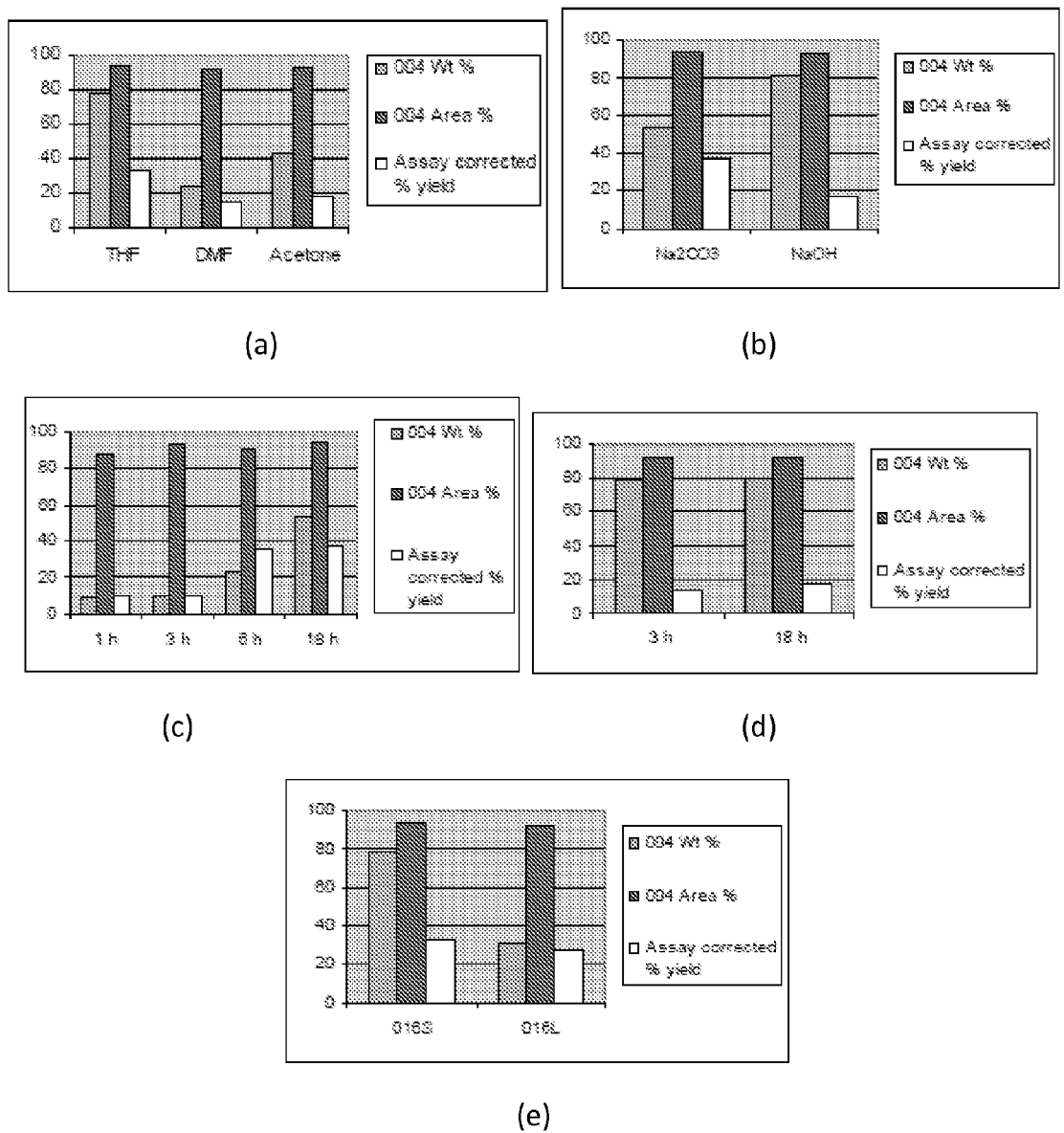
FIG. 16a-e shows tables of data for the scheme shown in FIG. 15 under variable conditions.

FIG. 16a shows that THF gave 4 (R=Et) in higher wt % purity and assay-corrected yield than the other tested solvents. THF was used as the solvent for further studies. The effect of base (sodium carbonate vs. sodium hydroxide) was also evaluated. FIG. 16b shows that sodium hydroxide produced 4 (R=Et) in higher wt % purity (80%); however, sodium carbonate gave higher assay corrected yield. Both wt % purity and assay-corrected yields were increased with increasing time, regardless of the base used FIGS. 16c and d. FIG. 16e shows that the use of 2 in solid form significantly increased 4 (R=Et) wt % purity compared to 4 (R=Et) made from an acetic acid solution of 2.

Figure 17:
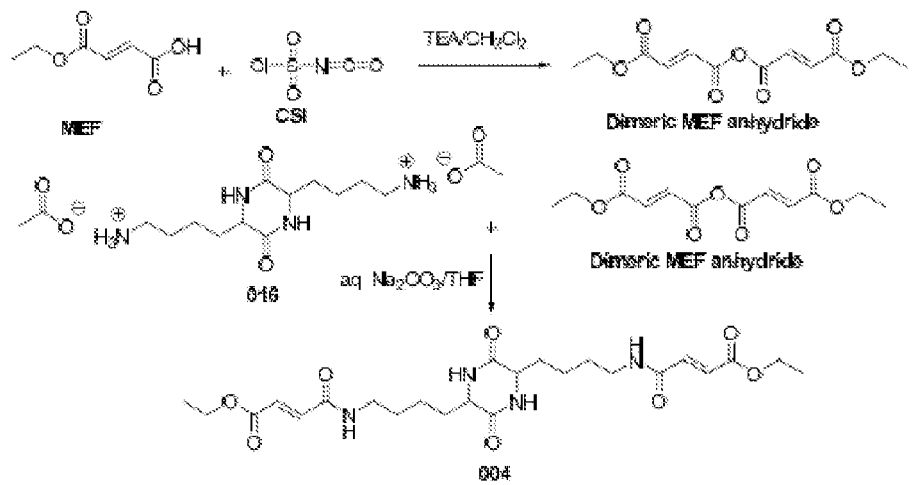
FIG. 17 is a chemical scheme showing the generation of MEF anhydride and subsequent reaction to give a substituted diketopiperazine.

FIG. 17 shows a chemical scheme for the generation of a dimeric MEF anhydride and subsequent reaction with an aminoalkyl-diketopiperazine.

Example

Dimeric MEF Anhydride Preparation

A 500 mL, 3-neck round bottom flask was equipped with a magnetic stirrer, temperature readout/controller, and an addition funnel with a nitrogen inlet. The exhaust gas was vented to a caustic scrubber. Monoethyl fumarate (MEF, 20 g), dry dichloromethane (DCM, 25 mL), and dry triethylamine (TEA, 20 mL) were charged to the flask. An exotherm was observed during TEA addition. The clear reaction mixture was cooled to −25° C. in a dry ice/acetone bath. A solution of chlorosulfonyl isocyanate (CSI, 9.8 g, 6.1 mL) in 10 mL of dry dichloromethane was added over 15-20 minutes. The temperature of the reaction mixture was maintained below 0° C. during addition. After the addition was complete, the reaction mixture was held below 10° C. for 6 hours. Water (200 mL) was added to the reaction flask. The layers were separated, and the aqueous phase was extracted with dichloromethane (2×200 mL). The organic phases were combined, dried over sodium sulfate, filtered and concentrated in vacuo. The resulting dimeric MEF anhydride was obtained in 94% yield and was used without further purification.

A 500 mL 3-neck round bottom flask was equipped with a magnetic stirrer, temperature readout/controller, and an addition funnel with a nitrogen head. The exhaust gas was vented to a caustic scrubber. The flask was charged with solid 2 (5.47 g) and a solution of sodium carbonate (8.80 g) in water (60 mL). THF (20 mL) was also added and the mixture was stirred until a clear solution was obtained. Dimeric MEF anhydride (8.97 g) was dissolved in THF (32 mL), and added to the reaction flask by addition funnel over 10-15 minutes. The reaction mixture was stirred at room temperature for 6 h.

The reaction mixture was quenched with water (50 mL) and stirring was continued for an additional 45 minutes. The resulting solids were collected by filtration, washed with water (2×50 mL) and acetone (50 mL), and dried in a vacuum oven at 50° C. overnight. The solids were analyzed using HPLC TM5466.

FIG. 18a-d shows the results for the synthesis of dimeric MEF anhydride when several conditions are varied. Solvent (a), CSI addition temperature (b), hold temperature after CSI addition (c), and reaction time (d) were explored. DCM appeared to provide superior results compared to THF.

Figure 18:
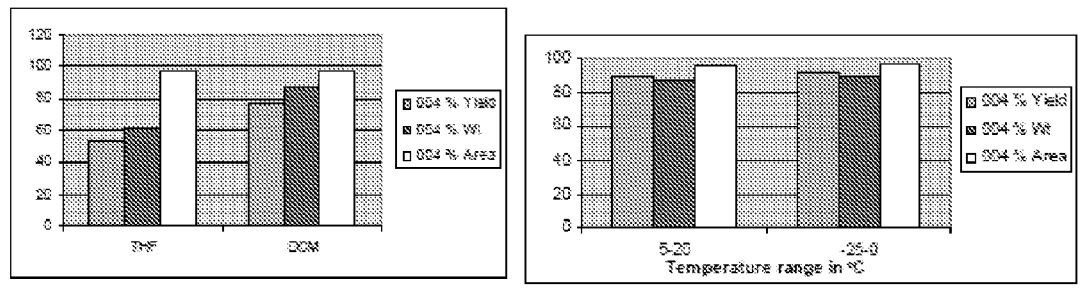
FIG. 18 shows the results for variable conditions used to generate MEF anhydride.
Figure 18:
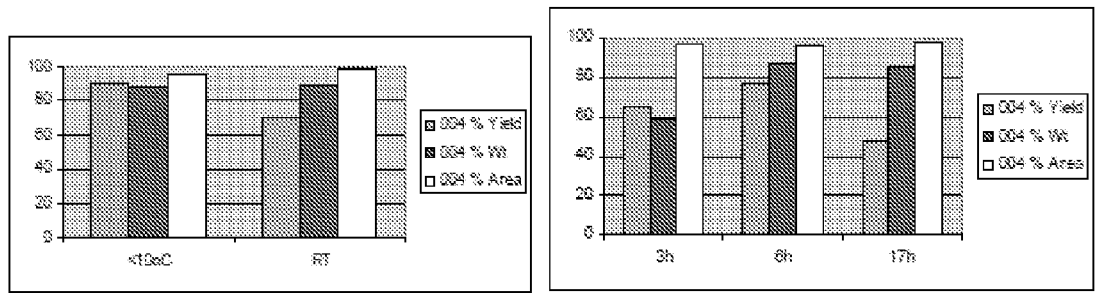

FIG. 18b shows the effect of CSI addition temperature. CSI addition was started at 5° C. and the reaction temperature was maintained below 20° C. throughout addition and CSI addition was started at −25° C. and the reaction temperature was maintained below 0° C. throughout addition. The temperature conditions for dimeric MEF anhydride preparation did not affect 4 yield and purity.

The reaction hold temperature after CSI addition was also explored (FIG. 18c). The results suggest that lower hold temperatures gave 4 in better yield with comparable purity. Different reaction times were explored FIG. 18d. The intermediate conditions tested (6 hours stirring) gave a good balance of 4 yield and purity. Short reaction times (i.e., 3 hours) were not sufficient for the reaction to complete, but extended times (i.e., 17 hours) permitted product degradation.

Taken together, the results suggested that the best conditions for dimeric MEF anhydride preparation included using DCM as the solvent, maintaining low temperatures during CSI addition, and holding for 6 h after CSI addition. Therefore, these conditions were used for further evaluation.

Parameters Screened for 4 Formation

Dimeric MEF anhydride was formed using the above conditions, and then converted to 4. The effects of various coupling conditions were evaluated and results shown in FIG. 19a-f. The condition variables include base choice, (a) solvent, (b) solvent-water ratio, reaction temperature and reaction time (c) and (d); $Na_2CO_3$ charge (e) and use of solid or liquid form for the amine (f).

Figure 19:
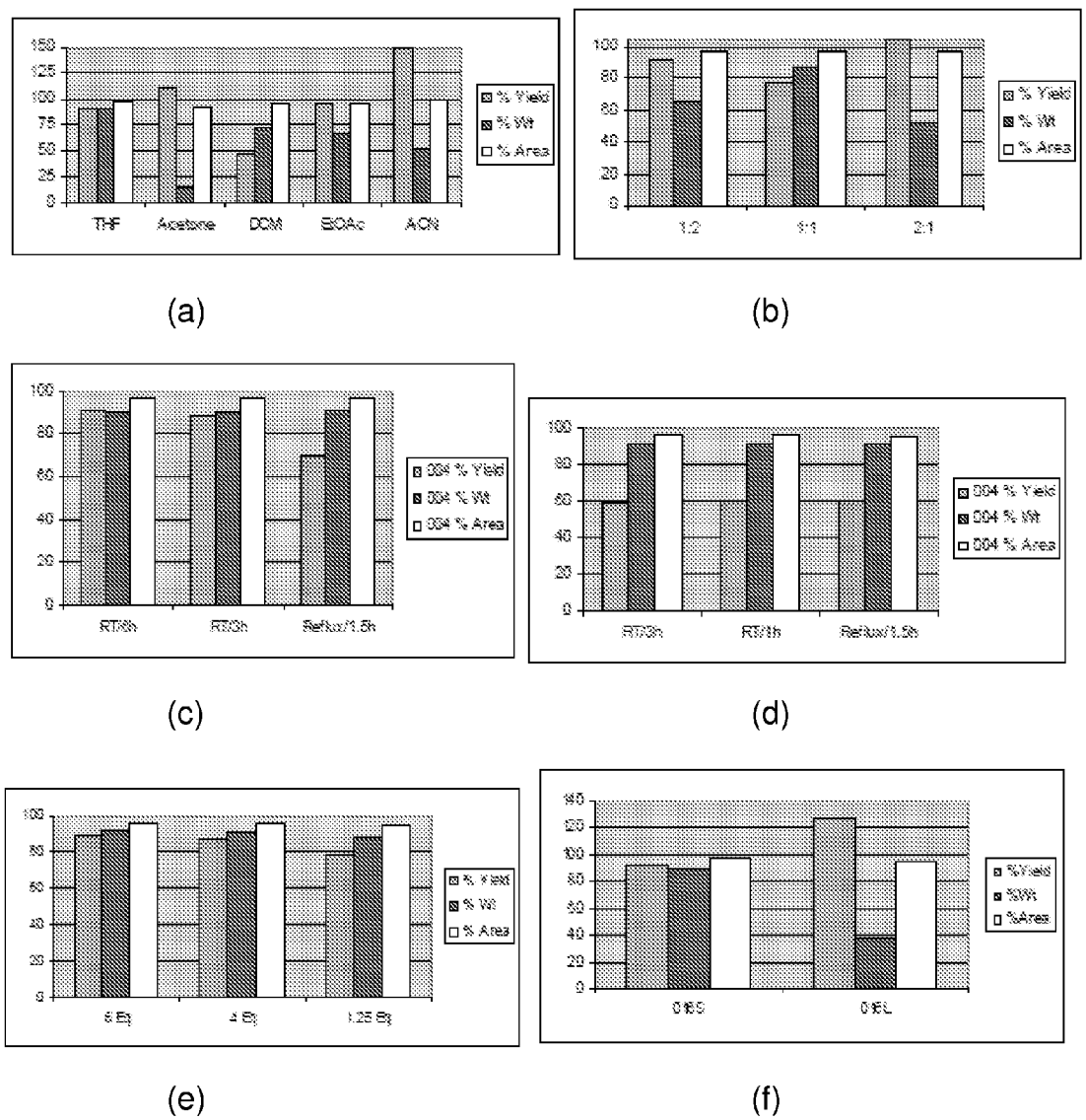
FIG. 19a-f shows the results for variable conditions used to react MEF anhydride to give a substituted diketopiperazine.

FIG. 19a shows the results where five solvents were evaluated: THF, acetone, DCM, ethyl acetate (EtOAc) and acetonitrile (ACN). THF gave 4 in higher yield and purity than the other tested solvents. In addition, several different water/THF mixtures were explored (FIG. 19b) because the reaction did not proceed well in the absence of water. The results suggested that 4 (R=Et) purity was maximized when a 1:1 THF/water ratio was used. Different reaction time and temperature combinations were also explored using two bases (sodium carbonate and sodium hydroxide). A reaction time of 3-6 hours at room temperature using $Na_2CO_3$ gave 4 (R=Et) in 90% yield with 88 wt % purity (FIG. 19c). Neither reaction time nor temperature affected 4 (R=Et) yield and purity when NaOH was used as the base, but yields were lower compared to $Na_2CO_3$ (FIG. 19d). In short, the highest 4 (R=Et) yield obtained during this study was ~91% with 90 wt % purity using solid 2. Using 2 as an aqueous acetic acid solution gave 2 in good yield (90%), but with low purity (51%).

Example

MEF Mixed Anhydride Preparation

A 1 L, 4-neck round bottom flask was equipped with a magnetic stirrer, temperature readout/controller, and an addition funnel with a nitrogen inlet. The exhaust gas was vented to a caustic scrubber. Monoethyl fumarate (MEF, 30 g), dichloromethane (DCM) or tetrahydrofuran (THF) (200 mL), and triethylamine (TEA, 45 mL) were charged to the flask. An exotherm was observed during the TEA addition. The clear reaction mixture was cooled to −25° C. in dry ice/acetone bath. A solution of pivaloyl chloride (39.2 g, 40 mL) in 20 mL of DCM or THF was added over 15-20 minutes. The reaction temperature was maintained below −10° C. during addition. After the addition was complete, the reaction mixture was slowly brought to room temperature and was stirred for two hours. The resulting solids were removed by filtration though celite. The filter cake was washed with DCM or THF (2×100 mL) and acetone (50 mL). The filtrate was concentrated in vacuo to give the MEF mixed anhydride in 96% yield. This material was used without further purification.

A 500 mL 3-neck round bottom flask was equipped with a magnetic stirrer, temperature readout/controller, and an addition funnel with a nitrogen head. The exhaust gas was vented to a caustic scrubber. The flask was charged with solid 2 (5 g) and a solution of sodium carbonate (8.72 g) in water (60 mL). THF (20 mL) was also added and solution was stirred until clear. The MEF mixed anhydride (8 g) was dissolved in THF (25 mL), and added to the reaction flask via addition funnel over 5-10 minutes. The reaction mixture was stirred at room temperature for 3 h, then quenched with water (100 mL) and stirred for an additional 30 minutes. The resulting solids were collected by filtration, washed with water (2×80 mL) and acetone (2×80 mL), and dried in a vacuum oven at 50° C. overnight. The solids were analyzed using HPLC TM5466. Reaction yield, wt % purity, and area % purity were monitored.

Figure 20:
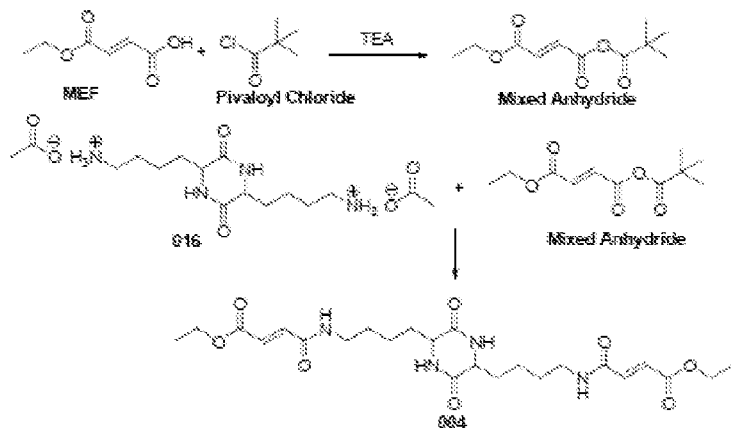
FIG. 20 is a chemical scheme showing the generation of a MEF mixed anhydride and subsequent reaction to give a substituted diketoipiperazine.
Figure 21:
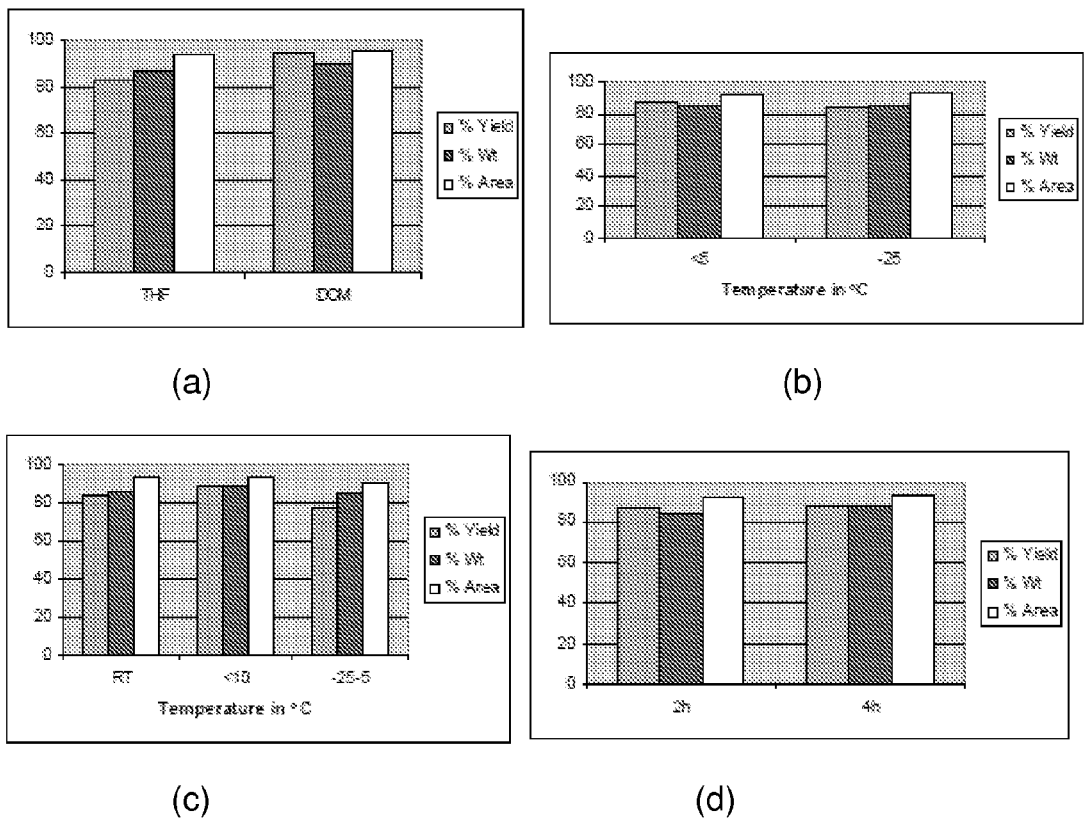
FIG. 21a-d shows the results for variable conditions used to generate a MEF mixed anhydride.

FIG. 20 shows a chemical scheme for the generation of a MEF mixed anhydride and subsequent reaction to give a substituted diketopiperazine.

FIG. 21a-d shows results for variable conditions used to generate a MEF mixed anhydride generally according to FIG. 20 and the effect on 4 (R=Et) production. (a) solvent, (b) pivaloyl chloride addition temperature, (c) hold temperature after pivaloyl chloride addition, and (d) reaction time were explored. Different combinations of pivaloyl chloride addition temperature, hold temperature and time were explored.

The results suggest that all the conditions tested gave 4 (R=Et) in comparable yield and purity.

Parameters Screened for 4 (R=Et) Formation

Figure 22:
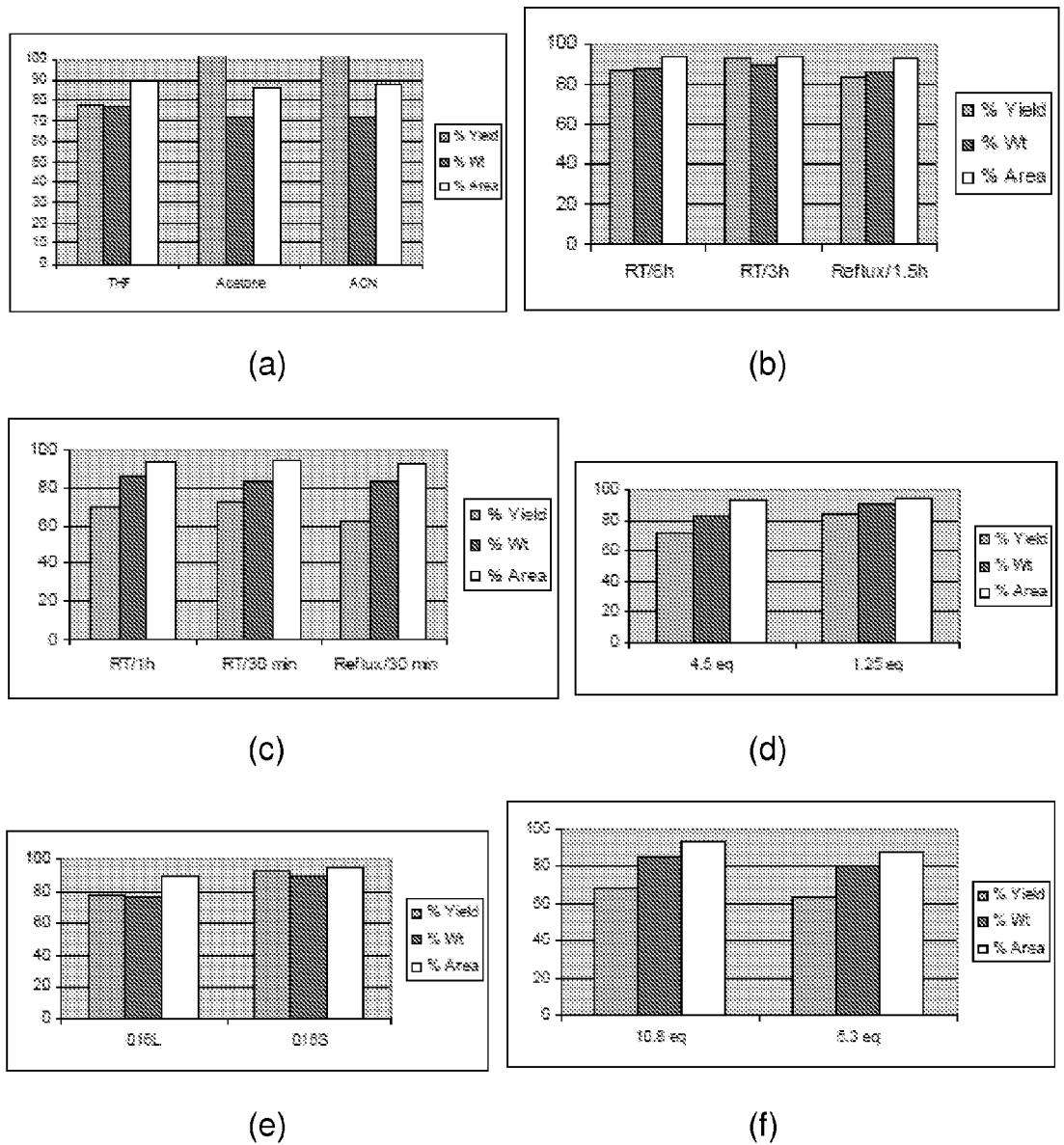
FIG. 22a-f shows the results for variable conditions used to react MEF mixed anhydride to give a substituted diketopiperazine.

MEF mixed anhydride was formed using the conditions described above, and then converted to 4 (R=Et). FIG. 22a-f shows the results where various coupling conditions were evaluated, including base choice, solvent, reaction temperature and reaction time. Three solvents were evaluated: THF, acetone, and acetonitrile (ACN). THF gave 4 (R=Et) in better purity than the other tested solvents (FIG. 22a). Different reaction time and temperature combinations were also explored using two bases (sodium carbonate and sodium hydroxide). A reaction time of 3 hours at room temperature using $Na_2CO_3$ gave 4 (R=Et) in 93% yield with 89 wt % purity (FIG. 22b). Lower yields and purities were obtained when NaOH was used as base (FIGS. 22c and d). The use of an aqueous acetic acid solution (2L) significantly decreased 4 (R=Et) yield and purity compared to use of 2 as a solid (FIG. 22e). Using NaOH instead of $Na_2CO_3$ as the 2L base resulted in even lower 4 (R=Et) yields; however, unlike the result observed with 2S, increasing the 2L sodium hydroxide charge increased 4 (R=Et) yield and purity (FIG. 22f vs. 22d).

Figure 23:
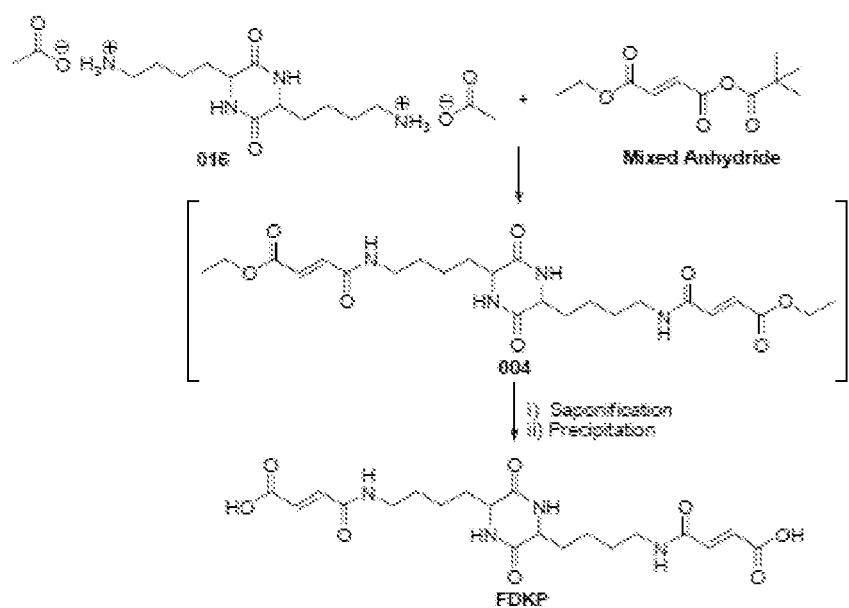
FIG. 23 shows a chemical scheme for the use of a MEF mixed anhydride for the generation of a substituted diketopiperazine and subsequent saponification of the MEF-moiety ester.

FIG. 23 shows a chemical scheme for the use of a MEF mixed anhydride for the generation of a substituted diketopiperazine and subsequent saponification of the MEF-moiety ester.

Preparation of 4 (R=Et) Using $Na_2CO_3$ as Base

A 500 mL 3-neck round bottom flask was equipped with a magnetic stirrer, temperature readout/controller, and an addition funnel with a nitrogen head. The exhaust gas was vented to a caustic scrubber. The flask was charged with solid 2 (5 g) and a solution of sodium carbonate (8.99 g) in water (60 mL). THF (20 mL) was also added and the solution was stirred until clear. MEF mixed anhydride (8 g) was dissolved in THF (25 mL), and added to the reaction flask via addition funnel over 5-10 minutes. The reaction mixture was stirred at room temperature for 3 h to facilitate in situ formation of 4 (R=Et). The reaction mixture was quenched with water (100 mL) and stirring was continued for an additional 30 minutes. Methanol (50 mL) was added to the reaction mixture and the reaction mixture was heated to reflux. Sodium hydroxide (5.45 g) solution in water (50 mL) was added to the reaction mixture via addition funnel over 5 minutes. The mixture was heated for about 10 minutes (until clear, an indication that 4 (R=Et) saponification was complete giving 4 (R=H)), and then cooled to 25° C. Concentrated HCl (35 mL) was added and reaction mixture was stirred for 2 hours at room temperature. The resulting solids were collected by filtration, washed with water (2×80 mL) and acetone (2×80 mL), and dried in a vacuum oven at 50° C. overnight. The solids were analyzed using HPLC TM5478. Reaction yield, wt % purity, and area % purity were monitored.

Preparation of 4 Using NaOH as Base

A 500 mL 3-neck round bottom flask was equipped with a magnetic stirrer, temperature readout/controller, and an addition funnel with a nitrogen head. The exhaust gas was vented to a caustic scrubber. The flask was charged with solid 2 (5 g) and a solution of sodium hydroxide (0.65 g) in water (60 mL). THF (20 mL) was also added and the mixture was stirred until clear. MEF mixed anhydride) (8 g) was dissolved in THF (25 mL), and added to the reaction flask via addition funnel over 5-10 minutes. The reaction mixture was stirred at room temperature for 30 minutes to facilitate in situ 4 formation, then quenched with water (100 mL) and stirred for an additional 30 minutes.

Methanol (50 mL) was added to the reaction mixture and the reaction mixture was heated to reflux. A solution of sodium hydroxide (4.75 g) in water (50 mL) was added to the reaction mixture via addition funnel over 5 minutes. The mixture was heated for approximately 10 minutes (until clear, an indication that saponification was complete giving 4 (R=H)), and then cooled to 25° C. Concentrated HCl (20 mL) was added and the reaction mixture was stirred for 2 hours at room temperature. The resulting solids were collected by filtration, washed with water (2×80 mL) and acetone (2×80 mL), and dried in a vacuum oven at 50° C. overnight. The solids were analyzed using HPLC TM5478. Reaction yield, wt % purity, and area % purity were monitored.

Parameters Screened for 4 (R=H) Formation

Figure 24:
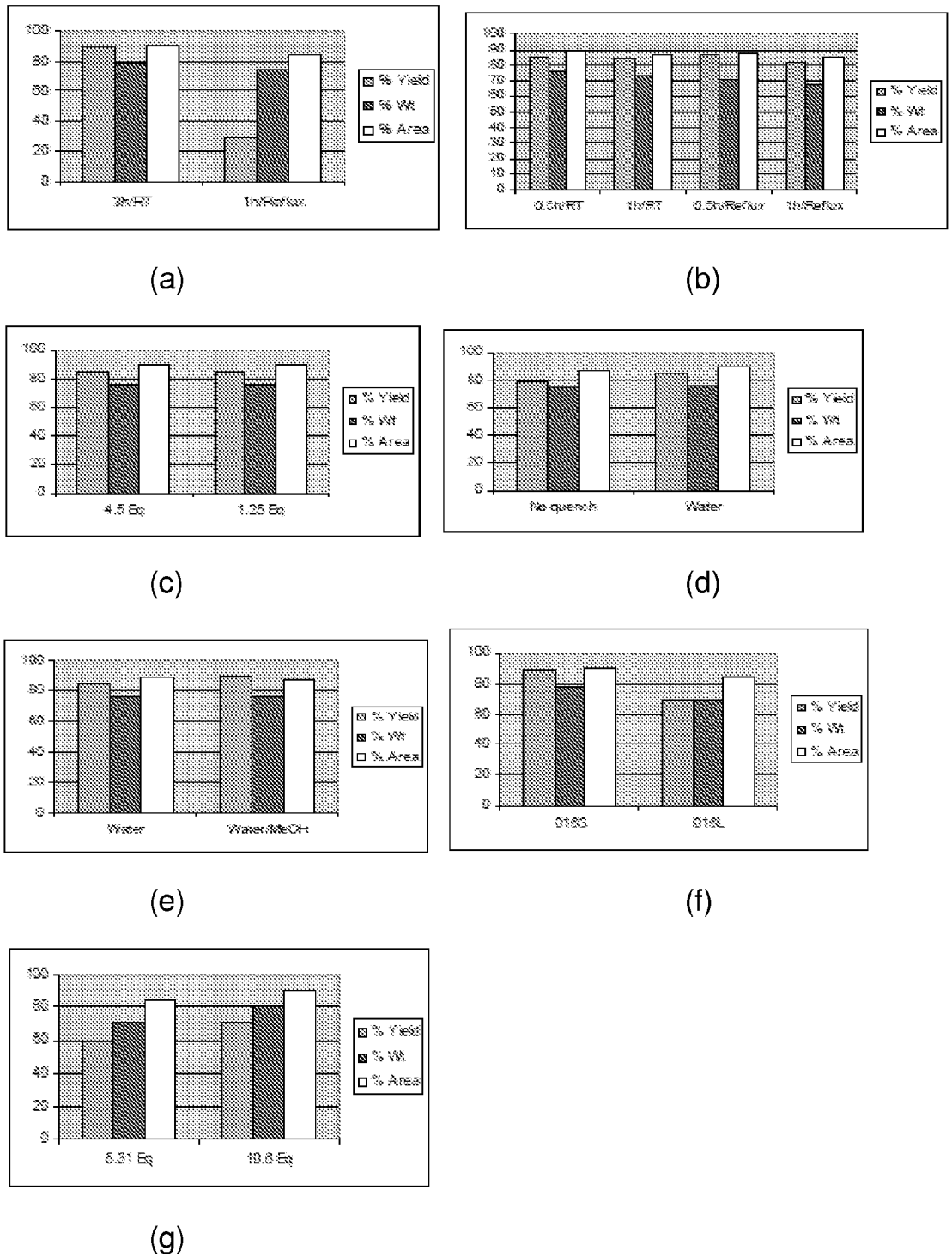
FIG. 24a-g shows results for variable conditions used in the synthesis of the saponified substituted diketopiperazine.

MEF mixed anhydride was prepared, 1 converted to in situ 4 (R=Et), and then to 4 (R=H) in a single reaction vessel. FIG. 24a-g shows results for the effects of various 4 (R=Et) coupling conditions, including base choice, reaction temperature and reaction time. Different reaction time and temperature combinations were explored using two bases (sodium carbonate and sodium hydroxide). A coupling reaction time of 3 hours at room temperature using $Na_2CO_3$ followed by saponification with sodium hydroxide gave 4 (R=H) in 89% yield and 78 wt % purity; increasing temperature and decreasing time decreased 4 (R=H) yield and purity (FIG. 24a). When NaOH was used as the coupling base, lower 4 (R=H) yield and purity were obtained with increasing reaction time at a fixed reaction temperature, and lower yield and purity were obtained with increasing reaction temperature at a fixed reaction time (FIG. 24b). Yield and purity were unaffected by NaOH charge (FIG. 24c). A slight decrease in yield was observed when the reaction was not quenched with water (FIG. 24d). Eliminating methanol from the saponification reaction did not affect 4 (R=H) yield or purity (FIG. 24e); however, reaction filtration suffered in the absence of methanol. The use of an 016 aqueous acetic acid solution (2L) decreased 4 (R=H) yield and purity compared to use of 2 solid (FIG. 24f). Using NaOH instead of $Na_2CO_3$ as the 016L base resulted in even lower 4 (R=H) yields; however, unlike the result observed with 2S, increasing the 2L sodium hydroxide charge increased 4 (R=H) yield and purity (FIG. 24g vs. FIG. 24c).

Figure 25:
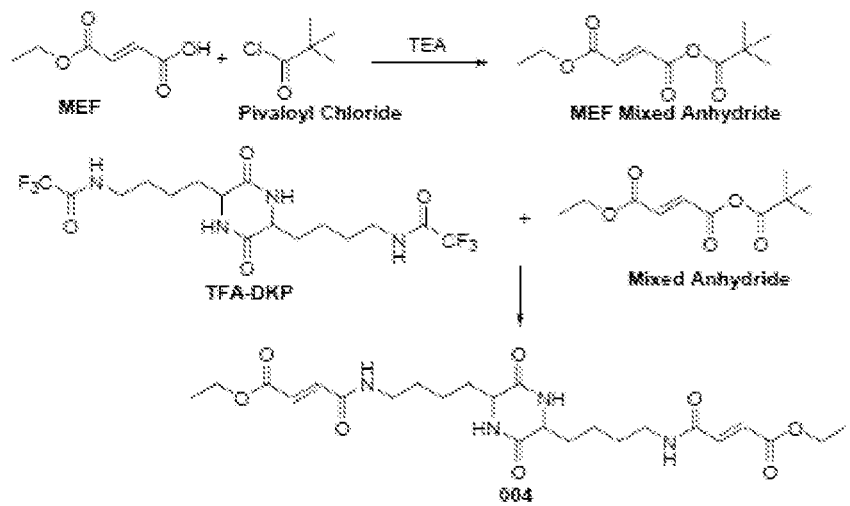
FIG. 25 shows a chemical scheme for the use of a MEF mixed anhydride for the generation of a substituted diketopiperazine after in situ deprotection of the diketopiperazine.

FIG. 25 shows a chemical scheme for the use of a MEF mixed anhydride for the generation of a substituted diketopiperazine after in situ deprotection of the diketopiperazine.

A 500 mL 3-neck round bottom flask was equipped with a magnetic stirrer, a temperature readout/controller, and an addition funnel with a nitrogen head. The exhaust gas was vented to a caustic scrubber. The flask was charged with TFA-DKP (5 g), THF (30 mL) and water (30 mL) and stirring was initiated. A solution of sodium hydroxide (1.20 g) in water (30 mL) was added and the solution was stirred for about 15 minutes (until clear, an indication that TFA-DKP deprotection was complete). The MEF mixed anhydride) (7.53 g) was dissolved in THF (30 mL) and added to the reaction flask via addition funnel over 5-10 minutes. The reaction mixture was stirred at room temperature for 30 minutes, then quenched with water (50 mL) and stirred for an additional 15 minutes. Acetone (15 mL) was added and the reaction mixture was stirred for additional 15 minutes. The resulting solids were collected by filtration, washed with water (2×70 mL) and acetone (3×70 mL), and dried in a vacuum oven at 50° C. overnight. The solids were analyzed using HPLC TM5466. Reaction yield, wt % purity, and area % purity were monitored. Assay-corrected yield was calculated by multiplying the yield by the wt % purity.

| Sample ID | % Yield | % Trans | % Area | % Wt |
|---|---|---|---|---|
| D698-45 | 84 | 18.81 | 95.57 | 86.28 |
| D698-47 | 86 | 27.74 | 95.28 | 85.15 |

TABLE 2

Analysis results of 004 obtained from coupling of TFA-DKP/mixed anhydride

| Sample ID | Reaction Conc.* | Solvent | % Yield | g per 1 L flask | % Trans | % Wt | % Assay corrected yield |
|---|---|---|---|---|---|---|---|
| D698-45 | 30 | THF | 84 | 19.08 | 18.81 | 86.28 | 72.5 |
| D698-47 | 30 | THF | 86 | 19.54 | 27.74 | 85.15 | 73.2 |
| D733-27T | 6.87 | THF | 99 | 39.48 | 66.07 | 68.47 | 67.8 |
| D733-23T | 5.86 | THF | 75 | 38.38 | 66.33 | 69.19 | 51.9 |
| D733-27A | 6.87 | Acetone | 88 | 35.04 | 54.58 | 75.06 | 66.1 |
| D733-23A | 5.86 | Acetone | 84 | 43.56 | 55.45 | 62.03 | 52.1 |

An MEF mixed anhydride was prepared and then coupled with deprotected TFA-DKP. The resulting crude 4 (R=Et) was obtained in 85% yield and 86 wt % purity. The trans isomer content was low; this was because the TFA-DKP starting material contained only the cis isomer. Solvent screening studies suggested that THF and Acetone gave comparable assay corrected yields. The trans isomer content increased with increasing reaction concentration and was highest when THF was used as the solvent.

Figure 26:
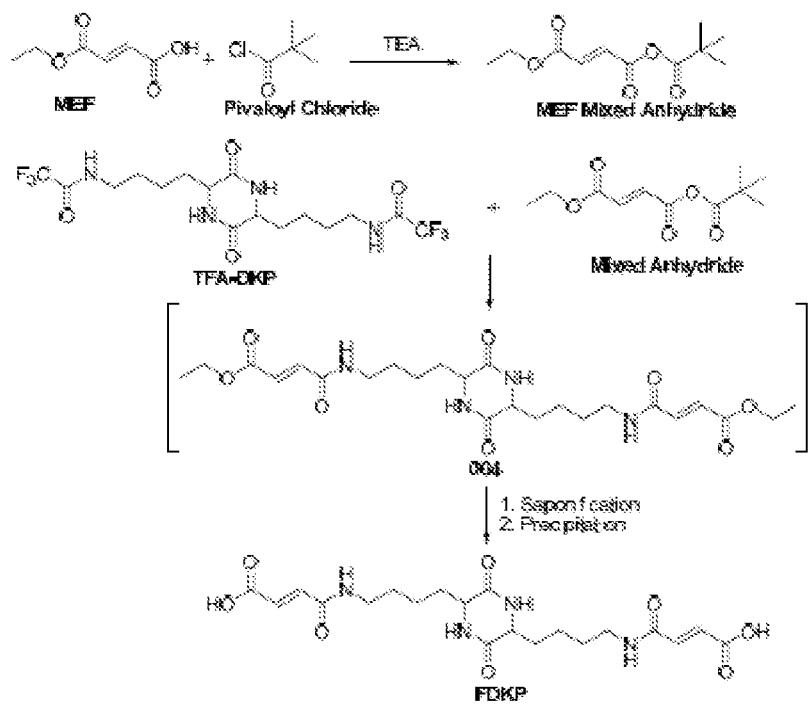
FIG. 26 shows a chemical scheme for the use of a MEF mixed anhydride for the generation of a substituted diketopiperazine after in situ deprotection of the diketopiperazine and subsequent saponification of the ester moiety.

FIG. 26 shows a chemical scheme for the use of a MEF mixed anhydride for the generation of a substituted diketopiperazine after in situ deprotection of the diketopiperazine and subsequent saponification of the ester moiety.

A 500 mL 3-neck round bottom flask was equipped with a magnetic stirrer, temperature readout/controller, and an addition funnel with a nitrogen head. The exhaust gas was vented to a caustic scrubber. The flask was charged with TFA-DKP (5 g), THF (30 mL) and water (30 mL) and stirring was initiated. A solution of sodium hydroxide (1.20 g) in water (30 mL) was added and the solution was stirred for about 15 minutes (until clear, an indication that TFA-DKP deprotection was complete). MEF mixed anhydride) (7.53 g) was dissolved in THF (30 mL), and added to the reaction flask via addition funnel over 5-10 minutes. The reaction mixture was stirred at room temperature for 30 minutes to facilitate fumaramide bond formation, then quenched with water (50 mL) and stirred for an additional 15 minutes. Methanol (50 mL) was added and the reaction mixture was stirred for additional 15 minutes. The reaction mixture was heated to reflux (~69° C.). Sodium hydroxide (4.00 g) in water (50 mL) was added to the reaction mixture via addition funnel over 5 minutes. The mixture was heated for about 10 minutes (until clear, an indication that saponification was complete), cooled to 25° C.

Concentrated HCl (30 mL) was added and reaction mixture was stirred for 2 hours at room temperature. The resulting solids were collected by filtration, washed with water (2×80 mL) and acetone (2×80 mL), and dried in a vacuum oven at 50° C. overnight. The solids were analyzed using HPLC TM5478. Reaction yield, wt % purity, and area % purity were monitored.

MEF mixed anhydride1 was synthesized, and then coupled with deprotected TFA-DKP, saponified, and precipitated in a single reaction vessel. The resulting crude 4 (R=H) was obtained in ~85% yield and ~75 wt % purity. The solvent used to make the mixed anhydride had no influence on crude 4 (R=H) quality.

| Sample Name | Solvent for anhydride | % Yield | % Trans | % Area | % Wt |
|---|---|---|---|---|---|
| 1 | THF | 87 | 53.9 | 87.67 | 75.54 |
| 2 | DCM | 85 | 53.7 | 87.88 | 75.59 |
| 3 | THF | 85 | 54.1 | 87.75 | 75.33 |
| 4 | DCM | 83 | 53.9 | 85.93 | 72.64 |

The following table shows data for recrystallized 4 (R=H) obtained from coupling TFA-DKP with MEF mixed anhydride. Specifications are shown in blue. Out of specification results are shown in red.

| Sample ID | % trans (53-63) | % Yield | % Wt ≥92 | 354 0.3 | 396 0.45 | 450A 0.3 | 466A 0.45 | 466B 0.15 | 484 0.75 | 788 0.45 | 806 0.20 |
|---|---|---|---|---|---|---|---|---|---|---|---|
| 5 | 75.8 | 84 | 92.0 | 0.09 | 0.01 | 0.06 | 0.02 | 0.85 | 0.10 | 0.32 | 0.01 |
| 6 | 61.5 | 79 | 92.6 | 0.09 | 0.03 | 0.04 | 0.01 | 0.02 | 0.09 | 0.56 | 0.01 |
| 7 | 62.2 | 70 | 91.7 | 0.11 | 0.03 | 0.04 | 0.01 | 0.98 | 0.17 | 0.58 | 0.05 |
| 8 | 61.5 | 69 | 92.0 | 0.07 | 0.01 | 0.04 | 0 | 0.72 | 0.09 | 0.55 | 0 |

The coupling of MEF mixed anhydride and TFA-DKP, followed by saponification and precipitation to crude 4 (R=H) in a single vessel, was evaluated. The resulting crude 4 (R=H) was obtained in good yield and purity. Crude 4 (R=H) recrystallization gave material in good purity (NLT 92 wt %).

The following tables show the results for coupling ethyl fumaroyl chloride and an aminoalkyl-diketopiperazine under varying conditions.

| Notebook Number | $Na_2CO_3$ Formula Multiplier | Water (7.0 mL/g $Na_2CO_3$) | Eq. Acid Chloride | Acetone (1 mL/1 mL water) | Addition Temp (° C.) | Hold Time After Addition (min) | Serial Wash Water, Acetone (mL/g 004 theo.) | Yield (%) | Area Percent Purity (%) |
|---|---|---|---|---|---|---|---|---|---|
| 470-123 | 1.05 | 75 | 6.0 | 75 | 25 | 30 | 0 | 86.8 | 70.47 |
| 470-125 | 1.00 | 71 | 3.0 | 71 | 25 | 180 | 10 | 54.8 | 63.97 |
| 470-127 | 1.05 | 75 | 6.0 | 75 | 25 | 180 | 10 | 70.3 | 70.78 |
| 470-132 | 1.00 | 71 | 6.0 | 71 | 25 | 30 | 10 | 64.3 | 76.28 |
| 470-134 | 1.05 | 75 | 3.0 | 75 | 10 | 30 | 0 | 76.8 | 66.45 |
| 470-138 | 1.00 | 71 | 3.0 | 71 | 10 | 30 | 10 | 61.8 | 61.59 |

-continued

| Notebook Number | Na₂CO₃ Formula Multiplier | Water (7.0 mL/g Na₂CO₃) | Eq. Acid Chloride | Acetone (1 mL/1 mL water) | Addition Temp (° C.) | Hold Time After Addition (min) | Serial Wash Water, Acetone (mL/g 004 theo.) | Yield (%) | Area Percent Purity (%) |
|---|---|---|---|---|---|---|---|---|---|
| 470-140 | 1.05 | 75 | 6.0 | 75 | 10 | 30 | 10 | 56.9 | 71.59 |
| 470-142 | 1.00 | 71 | 6.0 | 71 | 10 | 30 | 0 | 84.8 | 67.40 |

| Notebook Number | Na₂CO₃ Formula Multiplier | Water (7.0 mL/g Na₂CO₃) | Eq. Acid Chloride | Acetone (1 mL/1 mL water) | Addition Temp (° C.) | Hold Time After Addition (min) | Serial Wash Water, Acetone (mL/g 004 theo.) | Yield (%) | Area Percent Purity (%) |
|---|---|---|---|---|---|---|---|---|---|
| 470-147 | 1.05 | 75 | 3.0 | 75 | 25 | 180 | 0 | 92.8 | 62.96 |
| 470-163 | 1.00 | 71 | 6.0 | 71 | 10 | 180 | 10 | 57.4 | 73.68 |
| 470-150 | 1.00 | 71 | 3.0 | 71 | 10 | 180 | 0 | 82.4 | 60.19 |
| 479-159 | 1.05 | 75 | 3.0 | 75 | 25 | 30 | 10 | 67.9 | 66.30 |
| 470-161 | 1.00 | 71 | 3.0 | 71 | 25 | 30 | 0 | 85.9 | 65.69 |
| 470-172 | 1.00 | 71 | 6.0 | 71 | 25 | 180 | 0 | 97.2 | 67.38 |
| 470-174 | 1.05 | 75 | 6.0 | 75 | 10 | 180 | 0 | 94.4 | 67.88 |
| 470-176 | 1.05 | 75 | 3.0 | 75 | 10 | 180 | 10 | 73.7 | 70.31 |

The following table shows the results for varying the acid chloride concentration, hold time and wash.

| Notebook Number | Eq. Acid Chloride | Hold Time After Addition (min) | Serial Wash Water, Acetone (mL/g 004 theo.) | Yield (%) | Area Percent Purity (%) |
|---|---|---|---|---|---|
| 491-31 | 8.0 | 90 | 20 | 49.8 | 76.42 |
| 491-33 | 4.0 | 90 | 20 | 66.6 | 65.79 |
| 491-35 | 6.0 | 90 | 10 | 68.2 | 69.04 |
| 491-37 | 8.0 | 120 | 10 | 55.2 | 73.58 |
| 491-47 | 6.0 | 120 | 20 | 69.3 | 67.16 |
| 491-49 | 4.0 | 120 | 10 | 73.2 | 67.74 |
| 491-57 | 6.0 | 60 | 20 | 69.8 | 69.91 |
| 491-59 | 8.0 | 90 | 0 | 82.3 | 60.63 |
| 491-61 | 4.0 | 90 | 0 | 89.6 | 62.64 |
| 491-76 | 6.0 | 90 | 10 | 72.1 | 74.20 |
| 491-106 | 6.0 | 60 | 0 | 91.9 | 61.13 |
| 514-53 | 4.0 | 60 | 10 | 61.0 | 71.20 |
| 514-67 | 6.0 | 120 | 0 | 51.4 | 70.66 |
| 514-75 | 6.0 | 90 | 10 | 36.5 | 79.06 |
| 514-77 | 6.0 | 90 | 10 | 37.9 | 79.42 |
| 514-81 | 8.0 | 60 | 10 | 21.6 | 76.76 |

The following table shows the results from a coupling using sodium hydroxide under varying conditions.

| Notebook Number | NaOH (% excess) | Time after 016 addition (min.) | EFC (mol/mol 016) | Time after EFC (min) | Final acet/water ratio | Yield (%) | Purity (Area %) |
|---|---|---|---|---|---|---|---|
| 558-152 | 10 | 0 | 3 | 30 | 0.5 | 61 | 70.6 |
| 558-154 | 10 | 0 | 3 | 0 | 2 | 62 | 72.5 |
| 558-158 | 0 | 30 | 3 | 0 | 2 | 59 | 73.2 |
| 558-160 | 0 | 0 | 2 | 0 | 2 | 45 | 74.7 |
| 558-162 | 10 | 30 | 2 | 30 | 0.5 | 14 | 74.8 |
| 558-164 | 10 | 30 | 3 | 0 | 0.5 | 59 | 74.2 |
| 558-170 | 0 | 30 | 3 | 30 | 0.5 | 61 | 69.4 |
| 558-172 | 10 | 30 | 3 | 30 | 2 | 64 | 71.7 |
| 558-174 | 10 | 0 | 2 | 30 | 2 | 47 | 72.4 |
| 558-176 | 0 | 30 | 2 | 30 | 2 | 44 | 74.6 |
| 558-182 | 10 | 30 | 2 | 0 | 2 | 44 | 74.1 |
| 558-184 | 0 | 0 | 3 | 0 | 0.5 | 60 | 72.5 |
| 558-186 | 0 | 30 | 2 | 0 | 0.5 | 42 | 75.3 |
| 582-001 | 0 | 0 | 3 | 30 | 2 | 64 | 70.3 |
| 582-003 | 0 | 0 | 2 | 30 | 0.5 | 46 | 73.9 |
| 582-005 | 10 | 0 | 2 | 0 | 0.5 | 44 | 73.9 |

The following table shows further results using sodium hydroxide during coupling reactions.

| Notebook Number | RXN, Temp. (° C.) | H2O:016 ratio (mL/g 016) | Acetone:EFC ratio (mL/g EFC) | Yield (%) | Purity (Area %) |
|---|---|---|---|---|---|
| 582-014 | 30 | 30 | 30 | 44 | 78.7 |
| 582-016 | 10 | 30 | 30 | 57 | 78.8 |
| 582-018 | 10 | 5 | 30 | 40 | 75.1 |
| 582-020 | 30 | 30 | 0 | 42 | 75.2 |
| 582-026 | 10 | 30 | 0 | 60 | 73.3 |
| 582-028 | 30 | 5 | 0 | 16 | 83.7 |
| 582-032 | 30 | 5 | 30 | 26 | 76.6 |

Figure 27:
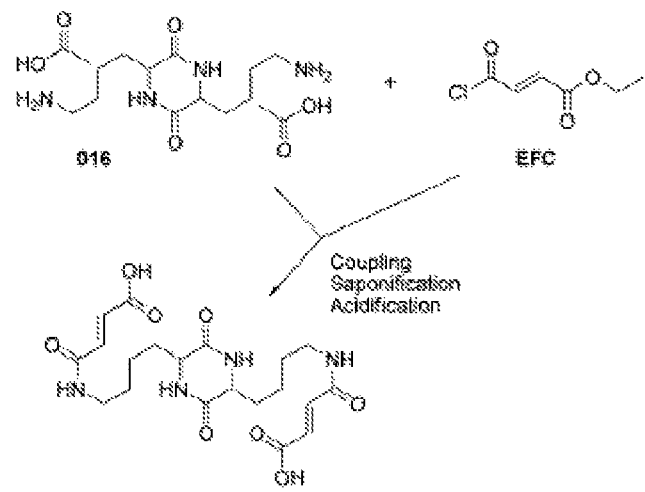
FIG. 27 is a chemical scheme showing the reaction between an aminoalkyl-diketopiperazine and EFC, followed by saponification of the ethyl moiety.

FIG. 27 is a chemical scheme showing the reaction between an aminoalkyl-diketopiperazine and EFC, followed by saponification of the ethyl moiety.

Saponification procedures: Fixed pH. A 500 mL 4-neck round bottom flask was charged with 26.75 g of an 18.68% 016 solution (5.00 g 016 real, 13.3 mmol) and 108 mL of water. Then, 15 mL of 9.5 M sodium hydroxide was added to the reaction. A solution of 4.6 mL (33 mmol, d=1.17) EFC in 125 mL of THF was added drop-wise by addition funnel, and the resulting mixture was held for 30 minutes to facilitate the coupling reaction. The reaction mixture was then treated with 10 mL of 9.5 M sodium hydroxide and heated to reflux (67° C.) to saponify. After 1.5 hours at reflux, the reaction was cooled to 30° C. and 15 mL (~150 mmol) of ~10M HCl was added. The reaction was stirred for 30 minutes. The resulting solids were collected by filtration, washed with water (3×50 mL), methanol (3×50 mL), and acetone (3×50 mL), and dried in a vacuum oven at 50° C. for a minimum of 15 hours. Weight percent purity was determined by TM54782.

Alternatively, reagent ratios were the same as described above with the following exceptions. For 2/EFC coupling, reaction was adjusted to pH 11 with 9.5 M sodium hydroxide. For saponification, additional 9.5 M NaOH was added to adjust the solution to a predetermined variable pH. Product precipitation was conducted as described above.

Figure 28:
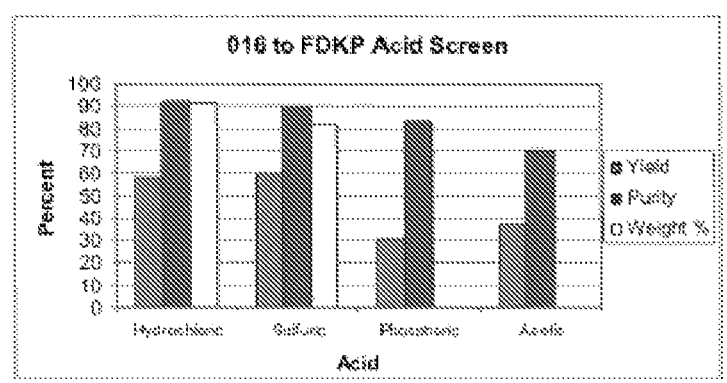
FIG. 28 shows the results for 4 acids used to precipitate the product shown in FIG. 27.

Four acids (hydrochloric, sulfuric, phosphoric, and acetic) were evaluated for 4 (R=H) precipitation. Hydrochloric acid gave the best product yield and quality (FIG. 28). Back-titration of 4 (R=H) precipitated with HCl demonstrated full conversion to the di-acid.

Figure 29:
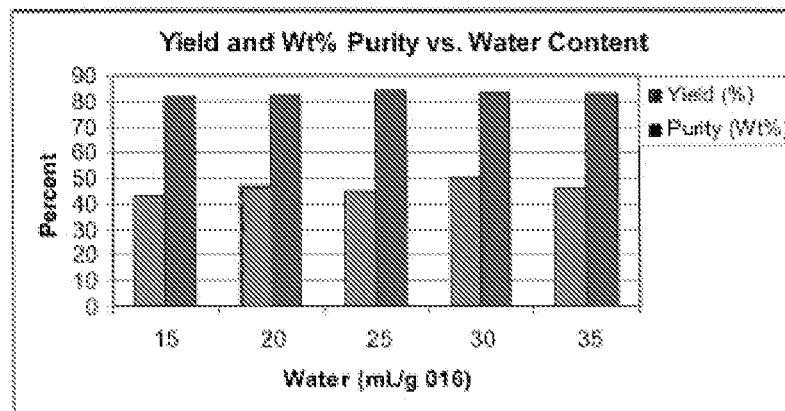
FIG. 29a-b shows results for variable conditions used to couple EFC with an aminoalkyl-diketopiperazine.
Figure 29:
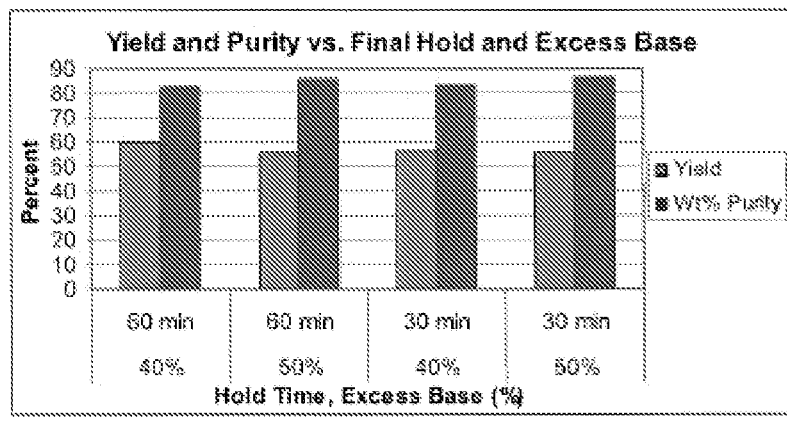

FIG. 29 shows the results for variable conditions used in the coupling reaction of FIG. 27.

Figure 30:
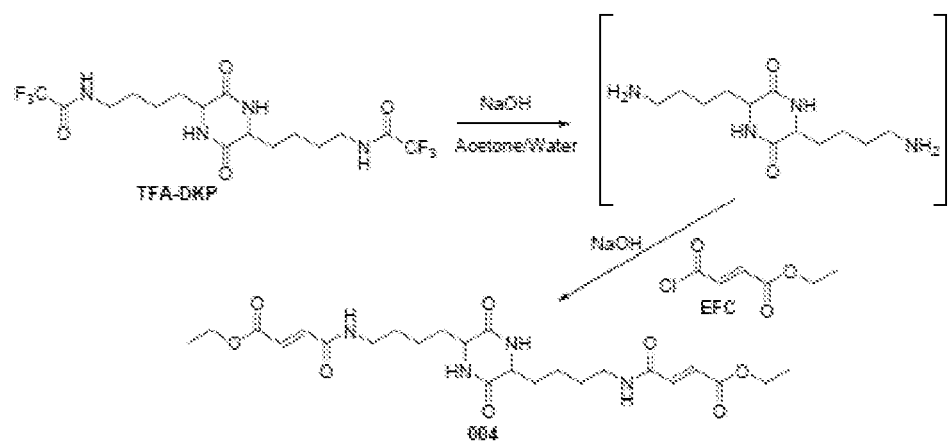
FIG. 30 shows a chemical scheme for in situ deprotection of an aminoalkyl-diketopiperazine followed by coupling with EFC.

FIG. 30 shows a chemical scheme for in situ deprotection of an aminoalkyl-diketopiperazine followed by coupling with EFC.

4 (R=Et) Preparation without pH Control:

A 500 mL 3-neck round bottom flask was equipped with a magnetic stirrer, temperature readout/controller, and an addition funnel with a nitrogen head. The exhaust gas was vented to a caustic scrubber. The flask was charged with TFA-DKP (9.68 g, 0.022 mol) and acetone (10 mL) and stirring was initiated. Sodium hydroxide (5.18 g, 0.13 mol) dissolved in water (25 mL) was added to the TFA-DKP slurry. An exotherm of ~13° C. was observed after the sodium hydroxide addition. The mixture was stirred at room temperature for about 10 minutes. The resulting clear yellow solution was pH 13. EFC (8.94 g, 0.055 mol) dissolved in acetone (10 mL) was added to the reaction mixture via addition funnel over 5-10 minutes. During the EFC addition, the mixture pH dropped to about 4, so additional sodium hydroxide (1.1 g, 0.028 mol) dissolved in water (10 mL) was added to raise the pH to about 9. The mixture was stirred at room temperature for about an hour, quenched with water (50 mL) and then stirred for an additional 30 minutes. The resulting solids were collected by filtration, washed with water (2×100 mL) and acetone (2×100 mL) and dried in a vacuum oven at 50° C. overnight. The solids were analyzed using HPLC TM5466. Reaction yield, and 4 (R=Et) area % and wt % purity were monitored.

4 (R=Et) Preparation Using pH Control:

A 500 mL 4-neck round bottom flask was equipped with a magnetic stirrer, a temperature readout/controller, a syringe pump for EFC addition, a pH probe and a syphon tube with adaptor for 25% NaOH attached to addition and stirring was initiated. Sodium hydroxide (4.32 g, 0.11 mol) dissolved in water (60 mL) was added to the TFA-DKP slurry. An exotherm of ~14° C. was observed after the sodium hydroxide addition. The mixture was stirred at room temperature for about 40 minutes. The resulting clear yellow solution was pH 11.9. EFC in acetone (18.38 g, 0.11 mol; prepared as above) was added to the reaction mixture via syringe pump over 20 minutes. The solution pH was held at 8.5 by addition of 25% NaOH using an addition pump. At the end of the EFC addition, the reaction pH was 9.7 and the reaction temperature was 50° C. The mixture was stirred at room temperature for about 30 minutes, quenched with water (100 mL) and then stirred for an additional 30 minutes. The resulting solids were collected by filtration, washed with water (2×100 mL) and acetone (2×100 mL) and dried in a vacuum oven at 50° C. overnight. The solids were analyzed using HPLC TM5466. Reaction yield, volume of base consumed, and 4 (R=Et) area % and wt % purity were monitored.

The coupling of deprotected TFA-DKP and EFC was conducted. When the reaction was conducted without pH control, the reaction mixture became acidic during the EFC addition. Additional NaOH was required to raise the pH to 7-8 and drive the reaction to completion. When the coupling reaction was conducted under pH control, crude 4 (R=Et) was obtained in 80% yield and 79.9 wt % purity. A second pH-controlled reaction was conducted, and evaluated use of neat EFC instead of an EFC/acetone solution. Here, the reaction pH at the end of the EFC addition was 4.4, in spite of the addition of 2.32 molar equivalents of NaOH (relative to EFC). These studies demonstrated that the pH controlled direct coupling of deprotected TFA-DKP and EFC gives crude 4 (R=Et) in better yield and purity than conditions that did not use pH controlled conditions.

The terms "a" and "an" and "the" and similar references used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of any and all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context. Furthermore, references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Having shown and described an embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

What is claimed is:

1. A method of preparing a diketopiperazine of Formula I (R=H or ethyl, n=3):
comprising:

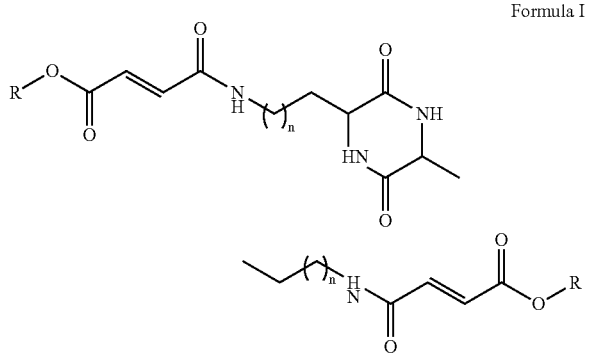

Formula I generating an aminoalkyl-diketopiperazine;
providing an activated derivative of monoethyl fumarate;
reacting the aminoalkyl-diketopiperazine with the activated monoethyl fumarate derivative; wherein the activated derivative is a mixed anhydride, the mixed anhydride resulting from the reaction of monoethyl fumarate and a reagent selected from the group comprising: diphenylphosphoryl azide, pivaloyl chloride, chlorosulfonyl isocyanate, and trifluoroacetic anhydride;
and wherein the activated derivative of monoethyl fumarate is reacted with the aminoalkyl-diketopiperazine in situ without purification.

2. The method of claim 1 further comprising the step of removing a protecting group from the aminoalkyl-diketopiperazine prior to reaction with the activated monoethyl fumarate.

3. The method of claim 1 wherein the mixed anhydride is generated by reacting monoethyl fumaroyl chloride with pivalic acid.

4. The method of claim 1 further comprising saponification of the ethyl esters of the diketopiperazine of Formula I.

5. The method of claim 1 further comprising isolation of the activated derivative of monoethyl fumarate before reacting with the aminoalkyl-diketopiperazine.

6. A method for the synthesis of an activated 4-nitrophenyl ester of mono-ethyl fumarate comprising:
in a first reaction mixture, providing ethyl fumaroyl chloride;
in a second reaction mixture, generating the salt of 4-nitrophenol by reacting with an appropriate base chosen from the group comprising: organic and inorganic metallic bases; and
combining the mixtures without purification.

7. The method of claim 6, wherein the base is an inorganic metallic base.

8. The method of claim 6, wherein the base is sodium hydroxide.

9. A method for the synthesis of a diketopiperazine of Formula I via a mixed anhydride of monoethyl fumarate comprising:
in a first reaction mixture, mixing monoethyl fumarate and a proton scavenger in an appropriate solvent;
adding an electrophile; and
using this mixture in the synthesis of the diketopiperazine of Formula I without purification.

10. The method of claim 9 wherein the electrophile is chosen from the group of:
diphenylphosphoryl azide, pivaloyl chloride, chlorosulfonyl isocyanate, trifluoroacetic anhydride, and monoethyl fumaroyl chloride.

11. The method of claim 9 wherein the proton scavenger is an organic amine.

12. The method of claim 9 wherein the solvent is a polar organic solvent.

* * * * *